(12) United States Patent
Wood et al.

(10) Patent No.: US 8,961,850 B2
(45) Date of Patent: Feb. 24, 2015

(54) METHOD OF MAKING A STRUCTURED SURFACE AND ARTICLE THEREFROM

(75) Inventors: Leigh E. Wood, Woodbury, MN (US); Timothy P. Pariseau, Forest Lake, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 112 days.

(21) Appl. No.: 13/805,896

(22) PCT Filed: Jun. 21, 2011

(86) PCT No.: PCT/US2011/041197
§ 371 (c)(1),
(2), (4) Date: Dec. 20, 2012

(87) PCT Pub. No.: WO2011/163193
PCT Pub. Date: Dec. 29, 2011

(65) Prior Publication Data
US 2013/0095281 A1 Apr. 18, 2013

Related U.S. Application Data

(63) Continuation-in-part of application No. 12/819,808, filed on Jun. 21, 2010.

(60) Provisional application No. 61/497,252, filed on Jun. 15, 2011.

(51) Int. Cl.
*B29C 53/02* (2006.01)
*B29C 55/00* (2006.01)
(Continued)

(52) U.S. Cl.
CPC .............. *B32B 3/06* (2013.01); *A44B 18/0065* (2013.01); *A61F 13/625* (2013.01); *B32B 3/266* (2013.01);
(Continued)

(58) Field of Classification Search
None
See application file for complete search history.

(56) References Cited

U.S. PATENT DOCUMENTS 3,192,589 A * 7/1965 Pearson .......................... 24/452
3,717,908 A 2/1973 Perina
(Continued)

FOREIGN PATENT DOCUMENTS

DE 102006038334 2/2008
EP 0755665 1/1997
(Continued)

OTHER PUBLICATIONS

International Search Report of PCT/US2011/041197, dated Nov. 18, 2011, 3 pages.

*Primary Examiner* — Jeffrey Wollschlager

(57) ABSTRACT

A method of making a structured surface is disclosed. The method includes providing a thermoplastic backing with multiple rows of upstanding elements. The upstanding elements include stems with proximal ends attached to the thermoplastic backing and distal caps, and each distal cap has an overhanging portion that extends beyond the stem in a first direction. For at least some of the multiple rows, an implement is passed between two adjacent rows, wherein the implement contacts the overhanging portion of at least some of the distal caps in the two adjacent rows such that at least part of the overhanging portion is turned in a second direction, different from the first direction. A structured surface that can be prepared by the method is also provided along with a fastening laminate that includes a carrier and the structured surface and an absorbent article that includes the fastening laminate. A tool useful for carrying out the method is also provided.

20 Claims, 4 Drawing Sheets

(51) Int. Cl.
   *B32B 3/06* (2006.01)
   *A44B 18/00* (2006.01)
   *A61F 13/62* (2006.01)
   *B32B 3/26* (2006.01)
   *B32B 3/30* (2006.01)
   *B32B 5/02* (2006.01)
   *B32B 7/12* (2006.01)
   *B32B 27/12* (2006.01)
   *B32B 27/32* (2006.01)

(52) U.S. Cl.
   CPC . *B32B 3/30* (2013.01); *B32B 5/022* (2013.01); *B32B 7/12* (2013.01); *B32B 27/12* (2013.01); *B32B 27/32* (2013.01); *B32B 2250/02* (2013.01)
   USPC ... 264/285; 264/167; 264/177.17; 264/210.1; 264/210.2; 264/211.12; 264/280; 264/284; 264/320; 264/322; 264/339; 264/288.4

(56) References Cited

U.S. PATENT DOCUMENTS

| | | | | |
|---|---|---|---|---|
| 3,770,359 | A * | 11/1973 | Hamano | 425/305.1 |
| 4,001,366 | A | 1/1977 | Brumlik | |
| 4,454,183 | A | 6/1984 | Wollman | |
| 4,775,310 | A | 10/1988 | Fischer | |
| 4,894,060 | A | 1/1990 | Nestegard | |
| 5,077,870 | A | 1/1992 | Melbye | |
| 5,256,231 | A | 10/1993 | Gorman | |
| 5,260,015 | A | 11/1993 | Kennedy | |
| 5,460,769 | A | 10/1995 | Kaneko | |
| 5,537,723 | A | 7/1996 | Yoshida et al. | |
| 5,607,635 | A | 3/1997 | Melbye | |
| 5,660,666 | A | 8/1997 | Dilnik | |
| 5,664,302 | A | 9/1997 | Thomas | |
| 5,679,302 | A | 10/1997 | Miller | |
| 5,692,271 | A | 12/1997 | Provost | |
| 5,749,129 | A | 5/1998 | Murasaki et al. | |
| 5,781,969 | A * | 7/1998 | Akeno et al. | 24/452 |
| 5,800,845 | A * | 9/1998 | Akeno et al. | 425/224 |
| 5,845,375 | A | 12/1998 | Miller | |
| 5,868,987 | A | 2/1999 | Kampfer | |
| 5,879,604 | A | 3/1999 | Melbye | |
| 5,913,482 | A * | 6/1999 | Akeno | 24/452 |
| 5,930,875 | A | 8/1999 | Schreiner | |
| 5,953,797 | A | 9/1999 | Provost et al. | |
| 5,957,908 | A | 9/1999 | Kline | |
| 5,961,761 | A * | 10/1999 | Heindel et al. | 156/163 |
| 6,000,106 | A | 12/1999 | Kampfer | |
| 6,039,911 | A | 3/2000 | Miller | |
| 6,054,091 | A | 4/2000 | Miller | |
| 6,106,922 | A | 8/2000 | Cejka et al. | |
| 6,132,660 | A * | 10/2000 | Kampfer | 264/167 |
| 6,146,369 | A | 11/2000 | Hartman | |
| 6,162,040 | A * | 12/2000 | Clune | 425/363 |
| 6,190,594 | B1 | 2/2001 | Gorman et al. | |
| 6,248,276 | B1 | 6/2001 | Parellada et al. | |
| 6,287,665 | B1 | 9/2001 | Hammer | |
| 6,357,087 | B1 | 3/2002 | Takizawa et al. | |
| 6,368,097 | B1 * | 4/2002 | Miller et al. | 425/367 |
| 6,406,468 | B1 | 6/2002 | Dilnik | |
| 6,470,540 | B2 | 10/2002 | Aamodt et al. | |
| 6,526,633 | B2 | 3/2003 | Provost et al. | |
| 6,540,497 | B1 * | 4/2003 | Fuda et al. | 425/174.2 |
| 6,546,604 | B2 * | 4/2003 | Galkiewicz et al. | 24/572.1 |
| 6,558,602 | B1 | 5/2003 | Melbye | |
| 6,575,953 | B2 | 6/2003 | Olson | |
| 6,588,073 | B1 | 7/2003 | Zoromski | |
| 6,592,800 | B1 * | 7/2003 | Levitt et al. | 264/479 |
| 6,627,133 | B1 * | 9/2003 | Tuma | 264/167 |
| 6,635,212 | B1 | 10/2003 | Melbye | |
| 6,678,924 | B2 | 1/2004 | Murasaki et al. | |
| 6,708,378 | B2 * | 3/2004 | Parellada et al. | 24/452 |
| 6,814,912 | B2 | 11/2004 | Ausen et al. | |
| 6,899,841 | B2 * | 5/2005 | Buzzell et al. | 264/167 |
| 6,994,698 | B2 | 2/2006 | Leak | |
| 7,048,527 | B2 * | 5/2006 | Bay et al. | 425/149 |
| 7,048,818 | B2 | 5/2006 | Krantz | |
| 7,052,636 | B2 * | 5/2006 | Ausen et al. | 264/145 |
| 7,052,638 | B2 | 5/2006 | Clarner et al. | |
| 7,125,400 | B2 | 10/2006 | Igaue | |
| 7,198,743 | B2 | 4/2007 | Tuma | |
| 7,214,334 | B2 | 5/2007 | Jens et al. | |
| 7,223,314 | B2 | 5/2007 | Provost | |
| 7,241,483 | B2 | 7/2007 | Ausen | |
| 7,275,290 | B2 | 10/2007 | Clarner et al. | |
| 7,373,698 | B2 | 5/2008 | Erdman | |
| 7,407,496 | B2 | 8/2008 | Petersen | |
| 7,444,722 | B2 | 11/2008 | McDaniel | |
| 7,670,522 | B2 | 3/2010 | Ausen | |
| 7,727,440 | B2 * | 6/2010 | Armela et al. | 264/177.17 |
| 7,785,095 | B2 * | 8/2010 | Clune et al. | 425/363 |
| 7,897,078 | B2 | 3/2011 | Petersen et al. | |
| 8,020,262 | B2 | 9/2011 | Oertel | |
| 2002/0016581 | A1 | 2/2002 | Kline | |
| 2003/0034583 | A1 | 2/2003 | Provost | |
| 2003/0049439 | A1 * | 3/2003 | Johansson et al. | 428/343 |
| 2003/0085492 | A1 * | 5/2003 | Schulte | 264/443 |
| 2003/0130644 | A1 | 7/2003 | Baker | |
| 2003/0145440 | A1 | 8/2003 | Ausen | |
| 2003/0182776 | A1 | 10/2003 | Ausen | |
| 2004/0121694 | A1 | 6/2004 | Shepard | |
| 2004/0187276 | A1 | 9/2004 | Seth et al. | |
| 2004/0261232 | A1 | 12/2004 | Kurtz, Jr. | |
| 2005/0079321 | A1 | 4/2005 | Tuman | |
| 2005/0091805 | A1 | 5/2005 | Armela et al. | |
| 2005/0132544 | A1 | 6/2005 | Seth et al. | |
| 2007/0039142 | A1 | 2/2007 | Petersen | |
| 2007/0134489 | A1 | 6/2007 | Neugebauer | |
| 2009/0217492 | A1 | 9/2009 | Gallant | |
| 2011/0147475 | A1 | 6/2011 | Biegler | |
| 2011/0151171 | A1 | 6/2011 | Biegler | |
| 2012/0151722 | A1 | 6/2012 | Hertlein | |
| 2012/0204383 | A1 | 8/2012 | Wood | |
| 2012/0330266 | A1 | 12/2012 | Zonneveld | |

FOREIGN PATENT DOCUMENTS

| EP | 1 774 866 | 4/2007 |
|---|---|---|
| EP | 2179671 | 4/2010 |
| JP | 2010-29532 | 2/2010 |
| WO | WO 94/02091 | 2/1994 |
| WO | WO 94/23610 | 10/1994 |
| WO | WO 96/19174 | 6/1996 |
| WO | WO 00-15069 | 3/2000 |
| WO | WO 01/68019 | 9/2001 |

* cited by examiner

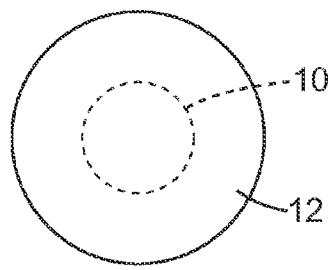
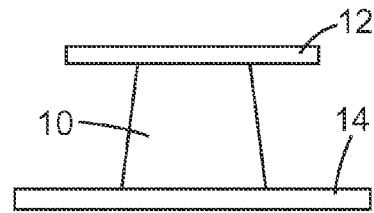
*Fig. 1A*  *Fig. 1B*
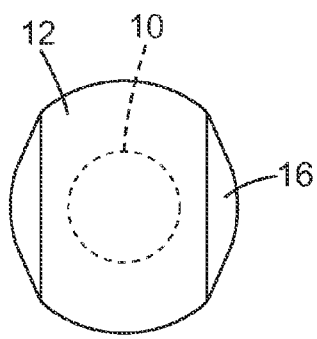
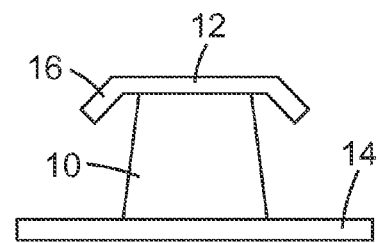
*Fig. 1C*  *Fig. 1D*
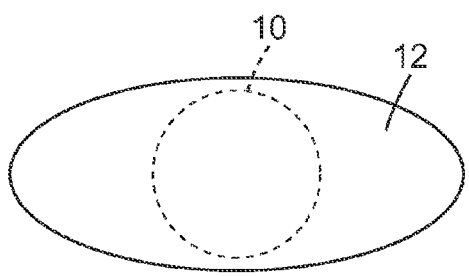
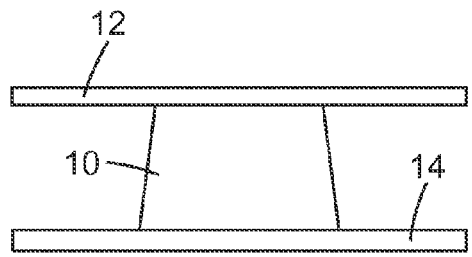
*Fig. 2A*  *Fig. 2B*
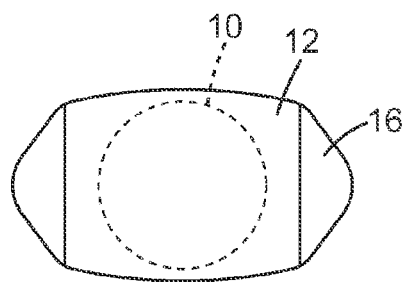
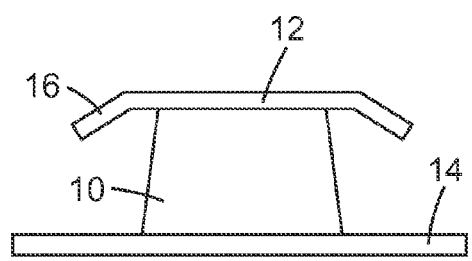
*Fig. 2C*  *Fig. 2D*

METHOD OF MAKING A STRUCTURED SURFACE AND ARTICLE THEREFROM

CROSS REFERENCE TO RELATED APPLICATIONS

This application is a national stage filing under 35 U.S.C. 371 of PCT/US2011/041197, filed Jun. 21, 2011, which is a continuation-in-part of U.S. application Ser. No. 12/819,808, filed Jun. 21, 2010, and claims priority to U.S. Application No. 61/497,252, filed Jun. 15, 2011, the disclosures of which are incorporated by reference in their entirety herein.

BACKGROUND

Articles with one or more structured surfaces are useful in a variety of applications (e.g., abrasive discs, assembly of automobile parts, and disposable absorbent articles). The articles may be provided as films that exhibit, for example, increased surface area, mechanical fastening structures, or optical properties.

Mechanical fasteners, which are also called hook and loop fasteners, typically include a plurality of closely spaced upstanding projections with loop-engaging heads useful as hook members, and loop members typically include a plurality of woven, nonwoven, or knitted loops. Mechanical fasteners are useful for providing releasable attachment in numerous applications. For example, mechanical fasteners are widely used in wearable disposable absorbent articles to fasten such articles around the body of a person. In typical configurations, a hook strip or patch on a fastening tab attached to the rear waist portion of a diaper or incontinence garment, for example, can fasten to a landing zone of loop material on the front waist region, or the hook strip or patch can fasten to the backsheet (e.g., nonwoven backsheet) of the diaper or incontinence garment in the front waist region. Mechanical fasteners are also useful for disposable articles such as sanitary napkins. A sanitary napkin typically includes a back sheet that is intended to be placed adjacent to the wearer's undergarment. The back sheet may comprise hook fastener elements to securely attach the sanitary napkin to the undergarment, which mechanically engages with the hook fastener elements.

The hooks of mechanical fastening systems may be formed with a curved shape or they may be substantially upright stems that are deformed to include, for example, a head in the shape of mushroom. Some methods, which have varying degrees of versatility and complexity, are available to control the shape of loop-engaging heads. See, e.g., U.S. Pat. No. 3,192,589 (Pearson); U.S. Pat. No. 5,953,797 (Provost et al.); U.S. Pat. No. 6,132,660 (Kampfer); U.S. Pat. No. 6,558,602 (Melbye et al.) and U.S. Pat. No. 6,708,378 (Parellada et al.) and U.S. Pat. App. Pub. No. 2002/0124359 (Murasaki et al.).

Hook and loop fastening systems can include at least two engagement strength characteristics: peel strength and shear strength. Peel strength corresponds to the force required to disengage the fastening members from one another by peeling one fastening member upward and away from the other fastening member. Shear strength corresponds to the force required to disengage the fastening members from one another by pulling at least one of the fastening members away from the other in a plane that is parallel to the fastening members. Typically, the engagement strength of the fastening members is higher in shear than in peel.

When a user wishes to separate the hook and loop fastening members (e.g., on an absorbent article such as a diaper), typically the user peels the fastening members apart. The ease with which the fastening members can peel apart affects the user's perception of the reliability of the attachment between the fastening members. For example, when a caregiver removes a diaper from a baby, if the hook strip feels like it peels too easily from the loop landing zone or backsheet of the diaper, the caregiver may question how well the fastening members can keep the diaper closed when it is in use. And in some instances low peel strength can result in inadvertent separation of the fastening members while the diaper is being worn.

Despite the progress in hook and loop fastening technology, an enhancement in the reliability of the attachment between the fastening members, whether actual or perceived, would be desirable.

SUMMARY

The present disclosure provides a method useful for readily changing the shape of distal caps on upstanding elements on a structured surface. Such distal caps may be, for example, loop-engaging caps of a mechanical fastener. The method includes passing an implement between adjacent rows of upstanding elements such that the implement contacts overhanging portions of at least some of the distal caps. Structured surfaces with upstanding elements having unique cap shapes can be achieved by this method. Also, depending on the initial shape of the upstanding elements, the method can provide a structured surface with improved peel strength when engaged with loop materials relative to comparable surfaces before treatment. The present disclosure also provides a fastening laminate and absorbent article that comprise the structured surfaces according to and/or made according to the present disclosure.

In one aspect, the present disclosure provides a method of making a structured surface. The method includes providing a thermoplastic backing with multiple rows of upstanding elements, the upstanding elements comprising stems with proximal ends attached to the thermoplastic backing and distal caps, wherein each distal cap has an overhanging portion that extends beyond the stem in a first direction. For at least some of the multiple rows, an implement is passed between two adjacent rows, wherein the implement contacts the overhanging portion of at least some of the distal caps in the two adjacent rows such that at least part of the overhanging portion is turned in a second direction, different from the first direction.

In another aspect, the present disclosure provides a structured surface. The structured surface includes a thermoplastic backing having an x-direction and a y-direction and upstanding elements having stems with proximal ends attached to the thermoplastic backing and distal caps. Each distal cap has overhanging portions that extend beyond the stem on all sides, wherein overhanging portions extending beyond the stem on all sides are equivalent in volume, and wherein for at least some of the upstanding elements the overhanging portions extending in only one of the x-direction or the y-direction are turned down toward the thermoplastic backing.

In some embodiments of the foregoing aspects, the structured surface is a mechanical fastener. Accordingly, in other aspects, the present disclosure provides a fastening laminate including a carrier and the structured surface according to and/or prepared according to the present disclosure, wherein the thermoplastic backing has a second surface opposite the upstanding elements, and wherein the second surface of the backing is joined to the carrier and an absorbent article having at least a front waist region, a rear waist region, and a longitudinal center line bisecting the front waist region and the rear waist region, wherein at least one of the front waist region or the rear waist region comprises such a fastening laminate.

In another aspect, the present disclosure provides a tool for shaping distal caps on upstanding elements on a structured surface, the tool comprising a template structured surface and multiple implements, the template structured surface comprising a template thermoplastic backing with multiple rows of template upstanding elements, wherein the template upstanding elements comprise stems with proximal ends attached to the template thermoplastic backing and distal tips, and wherein the multiple implements are positioned between the multiple rows of the template upstanding elements on the template structured surface.

In this application, terms such as "a", "an" and "the" are not intended to refer to only a singular entity, but include the general class of which a specific example may be used for illustration. The terms "a", "an", and "the" are used interchangeably with the term "at least one". The phrases "at least one of" and "comprises at least one of" followed by a list refers to any one of the items in the list and any combination of two or more items in the list. All numerical ranges are inclusive of their endpoints and non-integral values between the endpoints unless otherwise stated.

The terms "first" and "second" are used in this disclosure. It will be understood that, unless otherwise noted, those terms are used in their relative sense only. In particular, in some embodiments certain components may be present in interchangeable and/or identical multiples (e.g., pairs). For these components, the designation of "first" and "second" may be applied to the components merely as a matter of convenience in the description of one or more of the embodiments.

The term "row" refers to multiple upstanding elements lined up in a particular direction. The row or line of upstanding elements may be substantially straight. Each row contains multiple, spaced-apart, upstanding elements comprising stems with proximal ends attached to the thermoplastic backing and distal caps.

When it is said that an implement passes between two adjacent rows of upstanding elements, the path of the implement may be linear (that is, defined by two points in a line between two rows of upstanding elements). The path may also be substantially linear, which means that the path can have a slight curvature or slight oscillation. Some oscillation or curvature may result, for example, from continuous web processes as would be understood by a person skilled in the art. Any oscillation or curvature is such that the path of the implement generally does not have a portion that crosses over a row of hook elements.

A cut "through" the thermoplastic backing refers to a cut through the entire thickness of the backing.

The term "multiple" refers to more than one. In some embodiments, a structured surface, fastening laminate, absorbent article, or method according to the present disclosure having multiple rows of upstanding elements comprises at least 2, 4, 5, 6, 7, 8, 9, 10, 12, 14, 15, or 16 rows of upstanding elements.

The term "machine direction" (MD) as used above and below denotes the direction of a running, continuous web of the thermoplastic backing during the manufacturing of the structured surface. When a structured surface is cut into smaller portions from a continuous web, the machine direction typically corresponds to the y-direction of the structured surface. As used herein, the terms machine direction and y-direction are typically used interchangeably. The term "cross-direction" (CD) as used above and below denotes the direction which is essentially perpendicular to the machine direction. When a structured surface is cut into smaller portions from a continuous web, the cross direction corresponds to the x-direction of the structured surface.

For some embodiments, partial slits or partial-depth cuts are said to penetrate the thickness of the backing in a certain percent range. The percent penetration may be calculated as depth of the slit divided by the thickness of the backing, with the quotient multiplied by 100.

The term "nonwoven" when referring to a sheet or web means having a structure of individual fibers or threads which are interlaid, but not in an identifiable manner as in a knitted fabric. Nonwoven fabrics or webs can be formed from various processes such as meltblowing processes, spunbonding processes, spunlacing processes, and bonded carded web processes.

The term "elastic" refers to any material that exhibits recovery from stretching or deformation. Likewise, the term "nonelastic" refers to any material that does not exhibit recovery from stretching or deformation.

"Elongation" in terms of percent refers to {(the extended length–the initial length)/the initial length} multiplied by 100.

The above summary of the present disclosure is not intended to describe each disclosed embodiment or every implementation of the present disclosure. The description that follows more particularly exemplifies illustrative embodiments. It is to be understood, therefore, that the drawings and following description are for illustration purposes only and should not be read in a manner that would unduly limit the scope of this disclosure.

BRIEF DESCRIPTION OF THE DRAWINGS

The disclosure may be more completely understood in consideration of the following detailed description of various embodiments of the disclosure in connection with the accompanying drawings, in which:

FIG. 1A is a top view of an exemplary round distal cap on an upstanding element before contact with an implement in the method of the present disclosure;

FIG. 1B is a side view of the upstanding element of FIG. 1A before contact with an implement in the method of the present disclosure;

FIG. 1C is a top view of an exemplary round distal cap on an upstanding element after contact with an implement in the method of the present disclosure;

FIG. 1D is a side view of the upstanding element of FIG. 1C after contact with an implement in the method of the present disclosure;

FIG. 2A is a top view of an exemplary oval distal cap on an upstanding element before contact with an implement in the method of the present disclosure;

FIG. 2B is a side view of the upstanding element of FIG. 2A before contact with an implement in the method of the present disclosure;

FIG. 2C is a top view of an exemplary oval distal cap on an upstanding element after contact with an implement in the method of the present disclosure;

FIG. 2D is a side view of the upstanding element of FIG. 2C after contact with an implement in the method of the present disclosure;

DETAILED DESCRIPTION

Figure 3:
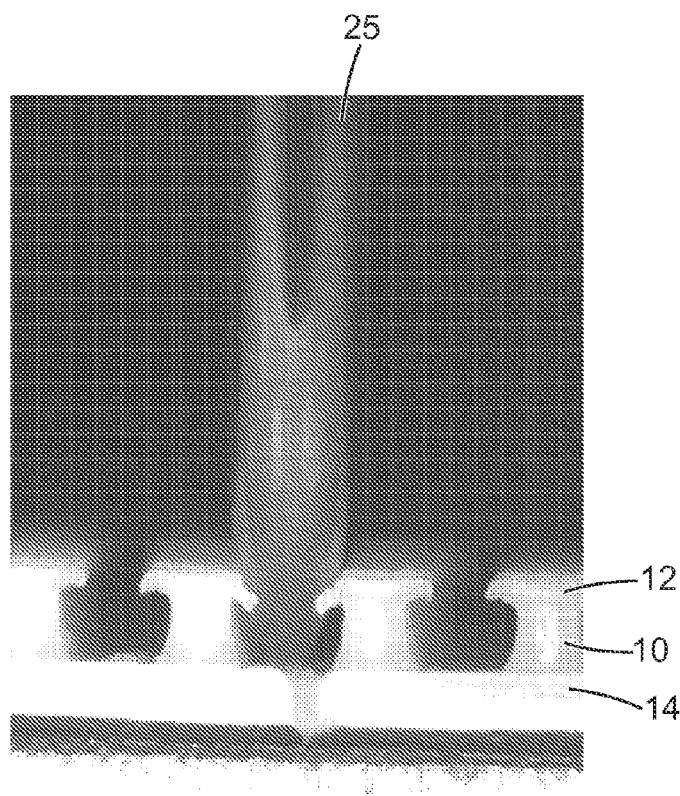
FIG. 3 is a photomicrograph of a side view of an implement passing between adjacent rows of upstanding elements according to some embodiments of a method of the present disclosure.

Reference will now be made in detail to embodiments of the disclosure, one or more examples of which are illustrated in the drawings. Features illustrated or described as part of one embodiment can be used with other embodiments to yield still a third embodiment. It is intended that the present disclosure include these and other modifications and variations.

FIGS. 1A and 2A illustrate top views of some embodiments of an exemplary distal cap 12 on an upstanding element of a structured surface before contact with an implement in the method of the present disclosure. FIGS. 1B and 2B illustrate side views of the embodiments shown in FIGS. 1A and 2A. The upstanding elements have stems 10 with proximal ends attached to the thermoplastic backing 14 and distal caps 12. The stem 10 typically has a cross-sectional area that is smaller than the area of the distal cap 12. The portion of the distal cap 12 that extends beyond the stem 10 is called the overhanging portion. In the illustrated embodiments, the upstanding elements have overhanging portions on all sides of the stems 10. In some embodiments, the distal cap 12 is round as shown in FIG. 1A, and in some embodiments, the distal cap 12 is oval as shown in FIG. 2A. Other distal cap shapes are also possible as described below. The upstanding elements may be said to be on the first surface of the backing 14. The first surface of the backing 14 is the top surface shown in FIGS. 1B and 2B. The surface to which the upstanding elements are attached can be called the first surface or the first major surface in any of the embodiments disclosed herein. As shown in FIGS. 1B and 2B, the overhanging portions extend beyond the stem 10 in at least a first direction. In the illustrated embodiment, the first direction is a direction generally parallel to the thermoplastic backing 14. In other embodiments of upstanding elements, the direction in which the overhanging portions extend may be at an angle to the thermoplastic backing. For example, the first direction may deviate from being parallel with the thermoplastic backing by up to 5, 10, or 20 degrees.

FIGS. 1C and 2C illustrate top views of some embodiments of an exemplary distal cap 12 on an upstanding element of a structured surface after contact with an implement in the method of the present disclosure. FIGS. 1D and 2D illustrate side views of the embodiments shown in FIGS. 1C and 2C. In the method according to the present disclosure, when the implement contacts the overhanging portion of at least some of the distal caps 12 as it is passed between two adjacent rows of upstanding elements, at least part of the overhanging portion 16 is turned in a second direction, different from the first direction. In the illustrated embodiments, the parts of the overhanging potions 16 that contact the implement are turned down toward the thermoplastic backing 14. The degree to which the overhanging portions 16 are changed from their original direction may depend, for example, on the type and size of the implement as well as other factors described below. The angle between the second direction and the first direction, which in the illustrated embodiment is the angle to which at least part of the overhanging portions 16 are turned toward the thermoplastic backing, may be in a range, for example, from 5 degrees to 90 degrees, 10 degrees to 75 degrees, or 20 degrees to 60 degrees. Although in the illustrated embodiments, distal caps 12 have overhanging portions on both sides of the stems 10 that are turned in a second direction, it is possible for structured surfaces according to and/or made according to the present disclosure to have parts of the overhanging portions 16 turned in a second direction on only one side of the stem 10, depending on whether an implement is used on both sides of the upstanding element.

The method according to the present disclosure includes passing an implement between two adjacent rows of upstanding elements. FIG. 3 is a photomicrograph of a side view of an implement 25 passing between adjacent rows of upstanding elements according to some embodiments of a method of the present disclosure. As shown in the illustrated embodiment, the implement 25 contacts the overhanging portion of at least some of the distal caps 12 in the two adjacent rows such that at least part of the overhanging portion is turned in a second direction, different from the first direction. In the illustrated embodiment, the part of the overhanging portion is turned toward the thermoplastic backing.

In the embodiment illustrated in FIG. 3, the implement 25 is a needle. The needle may be made of any suitable material (e.g., metal or polymer). In the illustrated embodiment, the needle is made of metal. In other embodiments, the implement may be, for example, a wire (e.g., stiff like a needle or more flexible like a guitar string) or a shim made of any suitable material.

Figure 4:
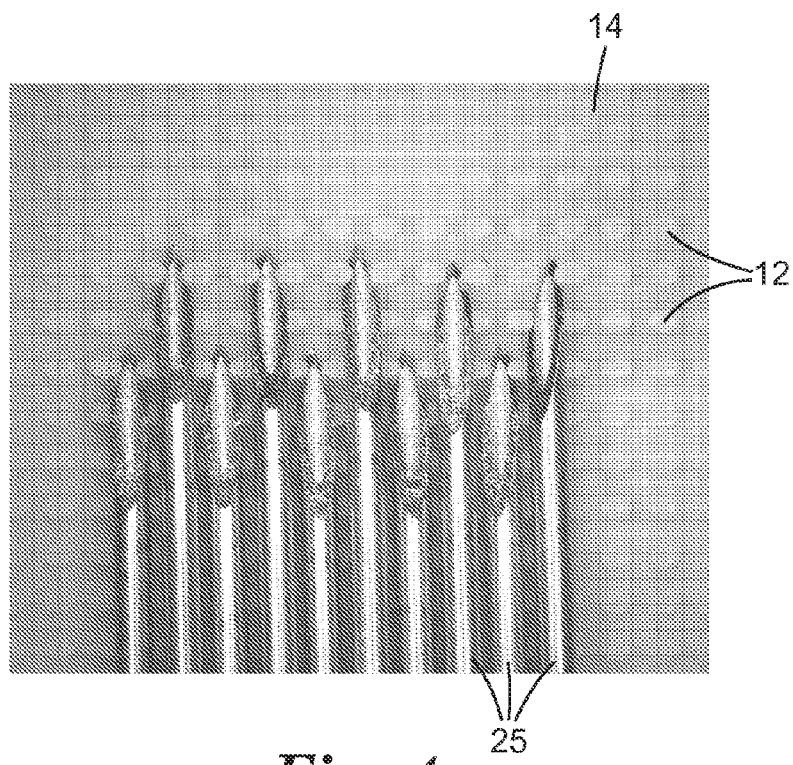
FIG. 4 is a photomicrograph of a top view of a structured surface being contacting with multiple implements with their tips not aligned with each other.

Referring now to FIG. 4, multiple implements 25 (needles as shown) are shown between multiple adjacent rows of upstanding elements on the thermoplastic backing 14. Use of multiple needles allows for the shaping of distal caps 12 in multiple rows simultaneously. The multiple implements can self-align between the multiple rows of upstanding elements on the thermoplastic backing 14, which may be made possible, for example, by the tapering of the tips of the needles and some flexibility in the needles.

Although in FIG. 4, an array of multiple implements 25 is shown positioned between multiple rows of upstanding elements such that, for at least a portion of the thermoplastic backing 14, the distal caps 12 of every row are contacted on each side, it is contemplated that not every row of distal caps 12 needs to by contact by an implement to produce useful structured surfaces. For example, an implement may be placed between every other row or every third row. Also, groups of multiple implements can be used to treat multiple rows of upstanding elements in one section or zone while adjacent sections or zones may remain untouched by the implements. Or different sections or zones of upstanding elements on a thermoplastic backing 14 may be contacted by implements having different sizes or shapes. Thus, the shaping of distal caps 12 in a structured surface may be tailored depending on the application requirements.

In FIG. 4, at least some of the multiple implements 25 have different lengths or are otherwise positioned such that their tips are not aligned with each other. This is not a requirement, and in some embodiments, the tips of the implements may be aligned with each other. In the illustrated embodiment, as the multiple implements are passed between the multiple rows, each distal cap 12 will be contacted by only one implement at a time although both sides of the distal caps 12 will be contacted sequentially. In this embodiment, a pinching of the distal caps 12 by contacting both sides at the same time may be avoided, which may be advantageous for some applications.

Figure 5:
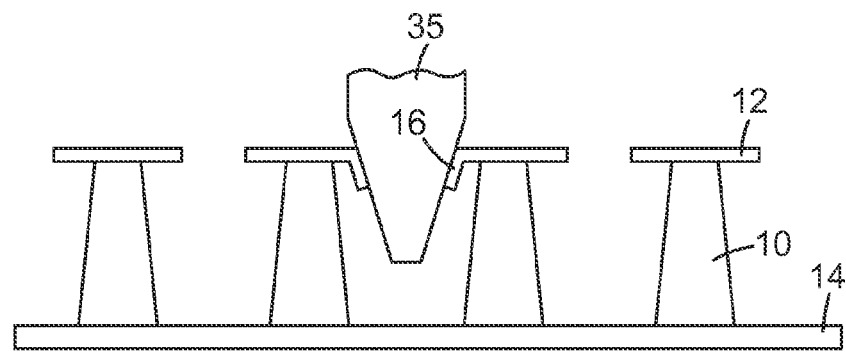
FIG. 5 is schematic side view of an implement with a tapered tip passing between adjacent rows of upstanding elements according to some embodiments of a method of the present disclosure.

In some embodiments, including the embodiments described above in which the implement is a needle, the implement is tapered. FIG. 5 illustrates how an implement 35 with a tapered tip may contact distal caps 12 in two adjacent rows of upstanding elements. The implement 35 contacts the overhanging portion 16 that extends beyond the stems 10 of the upstanding elements. In the embodiment illustrated in FIG. 5, the tapered portion of the implement 35 fits between adjacent rows of upstanding elements to contact the distal caps 12. As illustrated, the implement 35 does not need to touch the thermoplastic backing 14 to achieve the shaping effect.

Figure 6:
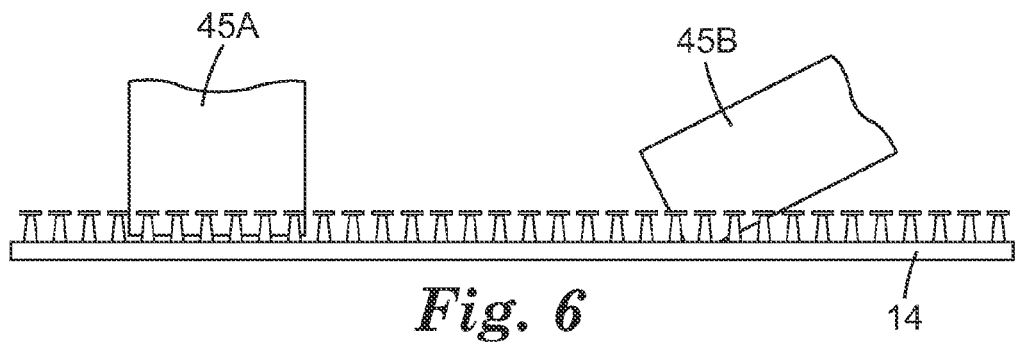
FIG. 6 is schematic side view of a structured surface being contacted with a shim implement according to some embodiments of a method of the present disclosure.

In the embodiment illustrated in FIG. 6, the implement is a shim 45A or 45B, which may be a metal shim, polymeric shim, or shim made from any suitable material and of any suitable shape. If the shim is flexible, multiple shims passed between multiple rows may self-align between the rows of upstanding elements. In the view shown in FIG. 6, the shim 45A or 45B is passed between the row of upstanding elements visible to the viewer and a row of upstanding elements behind that row, which is not visible to the viewer. Shim 45A is shown in an orientation in which it is placed perpendicular to the thermoplastic backing 14, with one edge is flat against or near the thermoplastic backing 14. Shim 45B is shown in an orientation in which it is placed at an angle to the thermoplastic backing 14, with only a corner of the shim 45B passing between the adjacent rows of upstanding elements. Suitable shims that may be useful for carrying out the present disclosure include standard feeler gauges, which may be tapered or have parallel sides.

In some embodiments, including the embodiments described above, the implement does not cut through the thermoplastic backing. In some of these embodiments, the implement does not cut through the thermoplastic backing in an interrupted manner such that a slit interrupted by bridging regions of the backing is formed. In some embodiments, the implement does not partially cut into the surface of the thermoplastic backing. As mentioned above, the implement does not even need to touch the thermoplastic backing in some embodiments.

In other embodiments, however, the implement may be a blade (e.g., rotary cutter) that may cut through or partially cut the thermoplastic backing while shaping the distal caps of upstanding elements on the thermoplastic backing.

In some embodiments, interrupted slits are cut into the thermoplastic backing by the implement (e.g., rotary cutter) between some pairs of adjacent rows of upstanding elements. The interrupted slits are interrupted by intact bridging regions of the backing. The bridging regions are regions where the backing is not cut through, and they are collinear with interrupted slit. The interrupted slits may be linear in the same direction as the multiple rows. The multiple portions of the backing on either side of the interrupted slits are typically abutting and not spaced apart after the rotary cutter passes between the multiple rows of upstanding elements. The interrupted slits may cut fully through the thickness of the thermoplastic backing, or they may partially cut into the first face of the thermoplastic backing (i.e., the same face from which the upstanding elements project) between some pairs of adjacent rows of upstanding elements. The partial slits may penetrate the thickness of the backing up to 5, 10, 20, 30, 40, 50, 60, 70, 80, or 90 percent, for example, in a range from 40 to 90 percent. Furthermore, the thermoplastic backing in the bridging regions may be uncut, or there may be partial-depth cuts in the thermoplastic backing in the bridging regions that do not extend through the thickness of the backing and are collinear with the interrupted slits. The partial-depth cuts may penetrate into the thickness of the backing up to 5, 10, 20, 30, 40, 50, 60, 70, 80, or 90 percent. The interrupted slits may be positioned between every row of upstanding elements, every other row of upstanding elements, or in other patterns that may be evenly spaced or unevenly spaced as desired.

For any of these embodiments that include bridging regions, the bridging regions may be aligned or staggered in a direction perpendicular to the direction of the interrupted slits. The bridging regions may be staggered such that a bridging region for one interrupted slit is located substantially midway between bridging regions in an adjacent interrupted slit. When the bridging regions are staggered in this manner, the number of bridging regions necessary to make the structured surface handle as an integral unit is minimized.

Furthermore, for any of these embodiments that include bridging regions, various lengths of bridging regions may be useful. In some embodiments, any bridging regions between a pair of adjacent rows have a combined length of up to 50 (in some embodiments, 40, 30, 25, 20, 15, or 10) percent of the length of the backing. In some embodiments, for maximizing the ability of the hook strip to bend, it may be desirable to minimize the combined length of the bridging regions. Minimizing the combined length of the bridging regions may be accomplished by at least one of minimizing the length of any particular bridging region or maximizing the distance between bridging regions. In some embodiments, the length of one bridging region is up to 3, 2, or 1.5 mm and at least 0.25, 0.5, or 0.75 mm. In some embodiments, the number of bridging regions is up to 1.5, 1.25, 1.0, 0.75, 0.60, or 0.5 per cm. The distance between bridging regions may be, for example, at least 0.75, 1.0, 1.25, 1.5, or 1.75 cm. Furthermore, the length of the interrupted slit or partial slit between bridging regions can be adjusted and is typically selected to maximize the distance between bridging regions. In some embodiments, the length of the interrupted slit or partial slit between bridging regions is at least 8 (in some embodiments, at least 10, 12, 14, 15, 16, 17, 18, 19, or 20) mm.

In some embodiments, partial slits are cut into the thermoplastic backing by the implement (e.g., rotary cutter) between some pairs of adjacent rows of upstanding elements. The partial slits may be linear in the same direction as the multiple rows. The partial slits may penetrate the thickness of the backing up to 5, 10, 20, 30, 40, 50, 60, 70, 80, or 90 percent, for example, in a range from 40 to 90 percent. When the partial slits penetrate the thickness of the backing in a range from 40 to 90 percent, the partial slits allow bending between the adjacent rows of upstanding elements, but the backing is not easily ruptured. In some embodiments, the partial slits penetrate the thickness of the backing in a range from 50 to 90, 50 to 85, 55 to 85, 60 to 80, or 65 to 80 percent. The partial slits may be positioned between every row of upstanding elements, every other row of upstanding elements, or in other patterns that may be evenly spaced or unevenly spaced as desired.

For any of the embodiments in which the implement is a blade that provides interrupted slits or partial slits in the thermoplastic backing, the structured surface may be in the form of a roll, from which patches are cut in a size appropriate to the desired application (e.g., for mechanical fastening). The bridging regions interrupting the interrupted slits allow the structured surface to be handled as an integral unit. Similarly, because the partial slits do not extend through the thermoplastic backing, the structured surface may be handled as an integral unit. The bridging regions in any of the embodiments that contain them or the uncut portion of the backing in the embodiments having partial slits allow structured according to and/or made according to the present disclosure to be handled in roll form and converted as desired.

In some embodiments, full slits are cut into the thermoplastic backing (i.e., through the entire backing thickness) by the implement (e.g., rotary cutter) between some pairs of adjacent rows of upstanding elements. In these embodiments, the structured surface is usually joined to a carrier as part of a fastening laminate as described in further detail below. The slits may be linear in the direction of the rows and extend from the top edge to the bottom edge of the backing to form separate, abutting strips of the thermoplastic backing on the carrier. The slits may be positioned between every row of upstanding elements, every other row of upstanding elements, or in other patterns that may be evenly spaced or unevenly spaced as desired.

Suitable thermoplastic materials for the backing and the upstanding elements in the method and structured surface disclosed herein include polyolefin homopolymers such as polyethylene and polypropylene, copolymers of ethylene, propylene and/or butylene; copolymers containing ethylene such as ethylene vinyl acetate and ethylene acrylic acid; polyesters such as poly(ethylene terephthalate), polyethylene butyrate and polyethylene napthalate; polyamides such as poly(hexamethylene adipamide); polyurethanes; polycarbonates; poly(vinyl alcohol); ketones such as polyetheretherketone; polyphenylene sulfide; and mixtures thereof. Typically, the structured surface is made of a polyolefin (e.g., polyethylene, polypropylene, polybutylene, ethylene copolymers, propylene copolymers, butylene copolymers, and copolymers and blends of these materials).

In the method and structured surface disclosed herein the thermoplastic backing and the upstanding elements are typically integral (that is, formed at the same time as a unit, unitary). Upstanding stems on a backing can be made, for example, by feeding a thermoplastic material onto a continuously moving mold surface with cavities having the inverse shape of the stems. The thermoplastic material can be passed between a nip formed by two rolls or a nip between a die face and roll surface, with at least one of the rolls having the cavities. The cavities may be in the inverse shape of a capped stem having a loop-engaging head or may be in the inverse shape of a stem without loop-engaging heads (e.g., a precursor to a fastening element). In the methods disclosed herein, the term "stem" is meant to include stems with or without loop-engaging heads, depending on the embodiment. Pressure provided by the nip forces the resin into the cavities. In some embodiments, a vacuum can be used to evacuate the cavities for easier filling of the cavities. The nip is typically sufficiently wide such that a coherent backing is formed over the cavities. The mold surface and cavities can optionally be air or water cooled before stripping the integrally formed backing and upstanding elements from the mold surface such as by a stripper roll. If the stems formed upon exiting the cavities do not have loop-engaging heads, loop-engaging heads could be subsequently formed into hooks by a capping method as described in U.S. Pat. No. 5,077,870 (Melbye et al.) and U.S. Pat. No. 5,845,375 (Miller et al.), the disclosure of which is incorporated herein by reference in its entirety. Typically, the capping method includes deforming the tip portions of the upstanding elements using heat and/or pressure. The heat and pressure, if both are used, could be applied sequentially or simultaneously.

Other suitable tool rolls include those formed from a series of plates defining a plurality of stem-forming cavities about its periphery such as those described, for example, in U.S. Pat. No. 4,775,310 (Fischer). Cavities may be formed in the plates by drilling or photoresist technology, for example. Still other suitable tool rolls may include wire-wrapped rolls, which are disclosed along with their method of manufacturing, for example, in U.S. Pat. No. 6,190,594 (Gorman et al.). Another exemplary method for forming a thermoplastic backing with upstanding elements includes using a flexible mold belt defining an array of upstanding stem-shaped cavities as described in U.S. Pat. No. 7,214,334 (Jens et al.). Yet other useful methods for forming a thermoplastic backing with upstanding stems can be found in U.S. Pat. No. 6,287,665 (Hammer), U.S. Pat. No. 7,198,743 (Tuma), and U.S. Pat. No. 6,627,133 (Tuma).

Some materials which may be useful precursors for the method according to the present disclosure and/or structured surface according to the present disclosure are commercially available, e.g., from 3M Company, St. Paul, under the trade designations "CS-600" or "CS-1010".

For the method of the present disclosure in any of its various embodiments, the thickness of the thermoplastic backing may be up to about 400, 250, 150, 100, 75 or 50 micrometers, depending on the desired application. In some embodiments, the thickness of the thermoplastic backing is in a range from 30 to about 225 micrometers, from about 50 to about 200 micrometers, or from about 100 to about 150 micrometers. In some embodiments, the upstanding elements have a maximum height (above the backing) of up to 3 mm, 1.5 mm, 1 mm, or 0.5 mm and, in some embodiments a minimum height of at least 0.05 mm, 0.1 mm, or 0.2 mm. In some embodiments, the upstanding elements have aspect ratio (that is, a ratio of height to width at the widest point) of at least about 2:1, 3:1, or 4:1.

For any of the embodiments of method and/or structured surface according to the present disclosure, the multiple rows of upstanding elements may be evenly spaced. For multiple rows that are evenly spaced, the spacing between multiple rows may differ by up to 10, 5, 2.5, or 1 percent.

In some embodiments of the method of making a structured surface according to the present disclosure, the upstanding elements have an initial density of at least 248 per square centimeter ($cm^2$) (1600 per square inch, $in^2$). For example, the initial density of the upstanding elements may be at least 394/$cm^2$ (2500/$in^2$), 550/$cm^2$ (3500/$in^2$), or at least about 787/$cm^2$ (5000/$in^2$). In some embodiments, the initial density of the upstanding elements may be up to about 1575/$cm^2$ (10000/$in^2$) or up to about 1182/$cm^2$ (7500/$in^2$). Initial densities in a range from 394/$cm^2$ (2500/$in^2$) to 1575/$cm^2$ (10000/$in^2$) may be useful, for example. However, the spacing of the upstanding elements need not be uniform. The initial density of the stems influences the thickness of the implement that is useful for passes between the rows of upstanding elements.

Various shapes of upstanding elements may be useful for practicing the present disclosure. The upstanding elements have distal caps with overhanging portions that extend beyond the stem in a first direction (in some embodiments, the x-direction or cross direction). The overhanging portions of the distal caps in the methods and structured surfaces according to the present disclosure are typically "loop-engaging". The term "loop-engaging" as used herein relates to the ability of an upstanding element on a structured surface disclosed herein to be mechanically attached to a loop material. The loop-engageability of uspstanding elements may be determined and defined by using standard woven, nonwoven, or knit materials. A region of upstanding elements with distal caps having loop-engaging overhangs generally will provide, in combination with a loop material, at least one of a higher peel strength, higher dynamic shear strength, or higher dynamic friction than a region of stems without loop-engaging heads. Upstanding elements that have distal caps with "loop-engaging overhangs" or "loop-engaging heads" do not include ribs that are precursors to hook elements (e.g., elongate ribs that are profile extruded and subsequently cut to form hook elements upon stretching in the direction of the ribs). Such ribs would not be able to engage loops before they are cut and stretched. Typically, upstanding elements that have distal caps with loop-engaging overhangs have a maximum thickness dimension of up to about 1 (in some embodiments, 0.9, 0.8, 0.7, 0.6, 0.5, or 0.45) millimeter.

Generally, upstanding elements with loop-engaging heads have a distal cap shape that is different from the shape of the stem. For example, the upstanding element may be in the shape of a mushroom (e.g., with a circular or oval head enlarged with respect to the stem), a hook, a palm-tree, a nail, a T, or a J. In some embodiments, the thermoplastic backing has an x-direction and a y-direction orthogonal to the x-direction. In some of these embodiments, at least part of the overhanging portion extends at a nonzero angle to y-direction (in some embodiments, the machine direction). The nonzero angle may be in a range from 30 to 90 degrees, 50 to 90 degrees, 60 to 90 degrees, 75 to 90 degrees, 80 to 90 degrees, or 85 to 90 degrees. In some embodiments, each distal cap has loop engaging overhangs extending in multiple (i.e., at least two) directions. In some of these embodiments, the distal caps have overhanging portions extending beyond the stems in both the x-direction and the y-direction. In some embodiments, the distal caps have overhanging portions that extend beyond the stems on all sides. In some embodiments, the upstanding element before treatment with the method disclosed herein comprises a stem with a mushroom head (e.g., the distal caps are round or oval before passing the implement between the two adjacent rows). The distal cap may also be angular (e.g., initially square or rhombus shaped before passing the implement between the two adjacent rows). In some embodiments, overhanging portions extending beyond the stem on all sides are substantially equivalent in volume (e.g., such as round or square distal caps). Substantially equivalent in volume means that the volume of material on all sides of the stem may be equal. However, there may be some variability due to the process of making upstanding elements on a backing as described above as would be understood by a person having ordinary skill in the art. The volume of material on all sides of the stem may differ, for example, up to about ten (in some embodiments, 5, 2.5, or 1) percent and be considered substantially equivalent in volume.

The method according to the present disclosure includes passing an implement between two adjacent rows of upstanding elements. At least a portion of the implement must be positioned between at least portions of upstanding elements in two adjacent rows. Accordingly, apparatus that are only designed to touch the tops of distal caps typically do not have any portion that actually is between two distal caps.

In some embodiments, the implement is pulled between adjacent rows of upstanding elements. In such embodiments, the method typically results in the overhanging portions that are contacted with the implement to be turned down toward the thermoplastic backing. In other embodiments, the implement is pushed between the adjacent rows of upstanding elements. In such embodiments, the method typically results in the overhanging portions that are contacted with the implement to be turned up away from the thermoplastic backing. In some embodiments, the implement is stationary and the thermoplastic backing is pulled under the implement. Depending on whether the pulling of the thermoplastic backing results in more of an upward or downward motion against the distal caps, the overhanging portions that are contacted with the implement may be turned away from the thermoplastic backing or down toward the thermoplastic backing, respectively.

In addition to the specific embodiments described above, the implement can be any suitable shape, as long as it can fit between two adjacent rows of upstanding elements. The implement can be, for example, a wire or needle with a circular cross-section (e.g., such as a guitar string) or non-circular cross-section. The implement should is typically large enough (i.e., with the appropriate thickness or diameter) to contact the overhanging portions of the distal caps without excessively pushing on the stems. The maximum thickness or diameter of the implement may be the spacing between the stems, which is typically larger nearer to the distal cap than at the proximal end attached to the thermoplastic backing. The method according to the present disclosure is useful with a variety of pin densities (density of upstanding elements) because, for example, the diameter or thickness of the implement(s) may be selected to adjust for different pin densities. Wires of various thicknesses or diameters can be selected depending on, for example, the spacing between the stems in the multiple rows, the size of the distal caps, the spacing between distal caps, and the desired amount of cap deflection in the second direction (in some embodiments, toward the backing). For example, an E guitar string may be useful when the density of upstanding elements is 550/cm$^2$ (3500/in$^2$). For increased spacings between the multiple rows, various B or G guitar strings may be useful. Similarly, various feeler gauges or needles of different sizes may be selected for the different structured surfaces.

The implement typically has sufficient strength to keep it from bending if it is pushed against the thermoplastic backing but advantageously has some flexibility to align between rows without destroying upstanding element. Flexibility in the implements typically allows them to stay in place between the adjacent rows even if there is some variability in the row spacing across the web of material being treated. Because of this effect, multiple implements used between multiple rows may be considered self-aligning, which may improve the robustness and reproducibility of this method.

The implement may be held perpendicular to the thermoplastic backing as it is passed between two adjacent rows but typically is positioned at an angle between 0 degrees and 90 degrees to the thermoplastic backing. In some embodiments, the implement is positioned at a 10 degree to 60 degree angle to the thermoplastic backing. In some embodiments, the implement is positioned at a 15 degree to 45 degree angle to the thermoplastic backing. Likewise, the pressure applied to hold the implement down while the thermoplastic backing is pulled under it, or it is pulled through the upstanding elements may vary. The pressure should be sufficient to keep the implement in contact with the distal caps. When multiple implements are used in the method according to the present disclosure, the length of the individual implements can be selected to provide the desired degree of flexibility for self-aligning and process robustness, without being too long to enable the needles or wires to easily get misaligned or crossed over each other. For smaller diameter wires or needles, this length may be advantageously shortened to provide the desired rigidity of the individual needles or wires. As shown above in FIG. 4, it is contemplated that the length of the individual needles or wires need not be all the same length. Additionally it is contemplated that the implement can be wire-like but with an end that has a different shape useful for shaping the overhanging portions of the distal caps.

In embodiments wherein the implement is a needle (e.g., hypodermic needle), including those embodiments described above and shown in FIGS. 3 and 4, the needle may additionally be useful for blowing cool air onto the thermoplastic backing to offset any heat generated by the friction of the needles with the overhanging portions of the distal caps. In other embodiments, needles may be useful for delivering a bead of pigment or adhesive, for example, for a particular end use.

In some embodiments of the method according to the present disclosure, the implement is a cutting blade (e.g., a rotary cutting blade). In these embodiments, in addition to shaping the distal caps, the implement provides slits in the thermoplastic backing. Interrupted slits can be made, for example, by using rotary cutting blades having gaps to form the bridging regions. The height of the blade in the gaps may be adjusted to allow for the bridging regions to be partially cut or not cut at all, depending on the desired embodiment. Partial slits can be made, for example, by adjusting the heights of the blades of the rotary die to make slits of the desired depth. For interrupted or non-interrupted slits through the entire thickness of the thermoplastic backing, the cutting may be performed from either surface of the continuous web, either the surface having the upstanding elements or the opposite surface. Typically, however, for slits through the thickness of the thermoplastic backing, slits are made in the same surface from which the upstanding elements project. Likewise, for partial slits, the slits are made in the same surface from which the upstanding elements project. It should be understood that rotary cutting methods disclosed herein on a continuous web may result in some instances with slits that cross over or cut through a row of upstanding elements. Although the rotary die, for example, may be positioned to form a slit between rows of upstanding elements, the variability in the web process and the rigidity of the rotary die may cause the slit to cross over a row of upstanding elements and later return to its intended position.

The method according to the present disclosure in any of its embodiments may be repeated multiple times (e.g., two or more times) to achieve the desired results. In such cases, the size and shape of the implements used in the first and subsequent applications of the method may be different, if desired. Furthermore, in some embodiments, the thermoplastic backing has a top edge and a bottom edge, and passing the implement between two adjacent rows of upstanding elements may be started at the top edge and continued to the bottom edge or any portion of the thermoplastic backing therebetween.

Figure 8A:
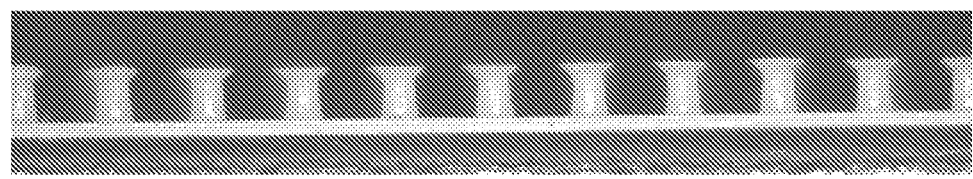
FIG. 8A is photomicrograph of a side view of multiple rows of upstanding elements before passing an implement between adjacent rows.
Figure 8B:
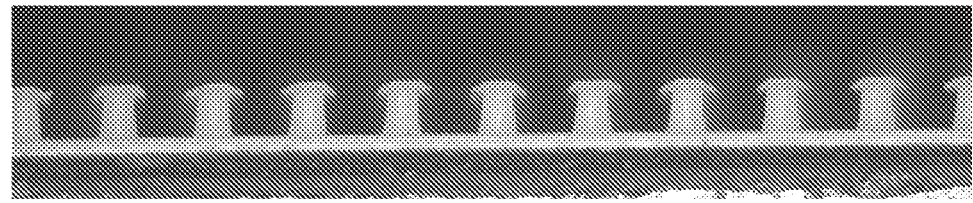
FIG. 8B is photomicrograph of a side view of multiple rows of upstanding elements after passing an implement between adjacent rows.

The method according to the present disclosure can provide structured surfaces with upstanding elements having distal caps with a unique shape. In some embodiments, the thermoplastic backing has an x-direction and a y-direction orthogonal to the x-direction where the distal caps have overhanging portions extending beyond the stem in both the x-direction and the y-direction, and the overhanging portions extending in only one of the x-direction or the y-direction are turned in the second direction. A photomicrograph of upstanding elements in a precursor material before application of the method of the present disclosure is shown in FIG. 8A, while the upstanding elements after treatment are shown in FIG. 8B. In some embodiments, the thermoplastic backing is a web of indefinite length having a machine direction and a cross direction. In embodiments wherein the thermoplastic backing is moved in the machine direction or the implement is moved only in the machine direction between rows of upstanding elements, only the overhanging portions extending in the cross direction are turned in the second direction.

Other methods of shaping distal caps of upstanding elements on a structured surface are known. For example, passing the upstanding elements through a gapped nip of a heated rubber roll and a backup roll causes the overhanging portions of the distal cap, that extend beyond the stem, to be pushed down toward the backing. This process is described in U.S. Pat. No. 6,132,660 (Kampfer). However, the rubber roll can wear, which causes changes in the process. Furthermore, the process can be rate limiting and is limited in how much the shape of the distal cap can be changed.

In contrast, the method according to the present disclosure does not require the use of rubber, which may rapidly degrade, and is easy to perform. Furthermore, the size and shape of the implement may be adjusted for versatility in shaping the distal caps.

Structured surfaces according to and/or made according to the methods described herein may have increased peel strength when engaged with a loop material than a comparable structured surface that is not treated. A comparable structured surface is the "same" as the structured surface disclosed herein, except that it has not been exposed to the method of the present disclosure. The comparable structured surface has the same dimensions (e.g., length, width, and thickness), the same density and height of upstanding elements, the same stem dimensions, the same configuration of upstanding elements (e.g., rows), and is made from the same material as the structured surface of the present disclosure. As shown in the Examples, below, the results may depend on the loop material used and the starting shape of the distal caps; however, the peel performance generally is increased using the methods described herein. In some embodiments, the improvement in y-direction or machine direction peel is most pronounced.

Structured surfaces according to some embodiments of the present disclosure have distal caps, wherein each distal cap has overhanging portions that extend beyond the stem on all sides, wherein overhanging portions extending beyond the stem on all sides are substantially equivalent in volume, and wherein for at least some of the upstanding elements the overhanging portions extending in only one of the x-direction or the y-direction are turned down toward the thermoplastic backing. Typically, the upstanding elements are aligned in rows on the thermoplastic backing. In these embodiments, the term "substantially equivalent in volume" has the same meaning as described above for the precursor material. The precursor material may have, for example, a round distal cap. The distal cap in the structured surface resulting from such a precursor material would have overhanging portions, some turned down and some not, that are rounded. In some embodiments of the structured surface, the thermoplastic backing is a web of indefinite length having a machine direction and a cross direction, wherein the y-direction is the machine direction, wherein the x-direction is the cross direction, and wherein only the overhanging portions extending in the cross direction are turned down toward the thermoplastic backing.

In some embodiments of carrying out the method disclosed herein, the multiple implements are positioned in a tool comprising a template structured surface, wherein the template structured surface comprises a template thermoplastic backing with multiple rows of template upstanding elements, the template upstanding elements comprising stems with proximal ends attached to the template thermoplastic backing and distal tips, and wherein the multiple implements are positioned between the multiple rows of the template upstanding elements on the template structured surface. In some embodiments of this tool, the implements comprise at least one of needles, wires, or shims. Typically, in such tools, the implements are positioned to extend from the tool for a distance suitable for carrying out the method disclosed herein.

Figure 7:
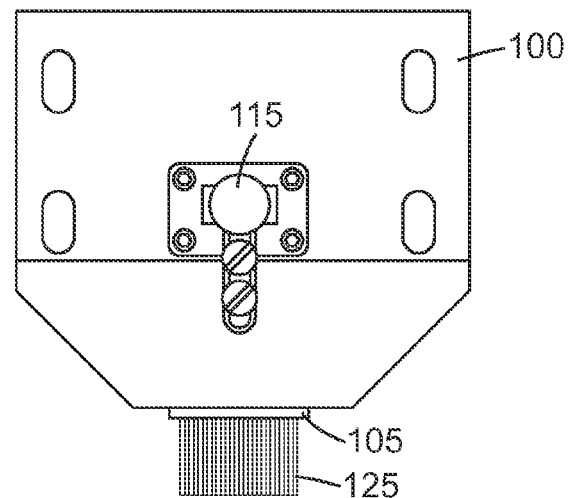
FIG. 7 is a photograph of an exemplary device useful for practicing the method of the present disclosure.

One embodiment of a tool for carrying out the method described herein is shown in FIG. 7. In FIG. 7, a series of hypodermic needles 125 is assembled to have the desired spacing to align with a desired structured surface. The desired spacing can be achieved, for example, by placing the needles into the rows of a stem web (not shown), which may be identical to the structured surface to be treated except that there are no distal caps on the stems. The stem web can be held to a piece of rubber with double stick tape (not shown), and after the needles 125 are positioned a second piece of rubber 105 is placed over them and the assembly placed in a clamp 100. The number of needles 125 can be adjusted to apply the method to the desired width of structured surface to be treated. By grasping the apparatus by handle 115, the method according to the present disclosure can be applied to structured surfaces by hand. The length of the needles 125 may be adjusted as described above. For example, the needles may extend beyond the rubber piece 105 by 0.5 cm to 5 cm, in some embodiments, 1 cm to 3 cm or 1.5 cm to 2.5 cm.

Other methods for positioning the implements are possible. For example, the template structured surface may have upstanding rails or ridges on a thermoplastic backing. Such a structured surface can be prepared, for example, by profile extrusion (e.g., using a method similar to that described in U.S. Pat. No. 4,894,060 (Nestegard). The implements can be placed between the rails or ridges.

Advantageously, the method according to the present disclosure does not require that the implement, upstanding elements, or thermoplastic backing be heated. Surprisingly, the method according to the present disclosure results in the permanent deformation of the contacted overhanging portions of the distal caps even in the absence of external heating. While no external heating is required, in some embodiments, it may be desirable to heat the implement and/or the thermoplastic backing. In some embodiments, it may be useful to apply the method of the present disclosure while the distal caps are still warm from a capping step that uses heat and pressure (e.g., such as that described in U.S. Pat. No. 5,077,870 (Melbye et al.) and U.S. Pat. No. 5,845,375 (Miller et al.)).

In embodiments wherein the distal caps are heated before or while contacting the implement, the heating is typically carried out below a melt temperature of the distal caps. When the thermoplastic material used to form the upstanding elements is a copolymer (e.g., copolymers of ethylene and propylene), the distal caps may have more than one melt temperature. In these embodiments, "below a melt temperature of the distal caps" means below at least one of the melt temperatures. Heating a thermoplastic web may be carried out, for example, in heated chamber such as an oven, or IR irradiation or hot air treatment may be used. In some embodiments, the structured surface may be heated in a range from 40° C. to 80° C. (in some embodiments, 50° C. to 60° C.) before being contacted with an implement. In embodiments wherein the implements are needles, hot air may be introduced through the needles to heat the implement and/or the structured surface while the distal caps are contacted with the implements. In other embodiments, the implements may be heated wires or heated shims.

In some embodiments, the method according to the present disclosure includes stretching the thermoplastic backing in at least one direction. Stretching may be most advantageous after contacting the distal caps with the implement or implements. Stretching can also be done before contacting the distal caps with the implement or implements, but row spacing variability may be increased as a result of stretching.

Stretching a thermoplastic backing with upstanding elements may be useful, for example, for reducing the cost of the resulting structured surface, which may be a mechanical fastener. However, there is also a potential reduction in performance as a result of reduced number of upstanding elements (e.g., hook elements) per unit area. The method of the present disclosure may be useful, for example, for offsetting the potential loss of performance from reducing the density of upstanding elements by increasing the percentage of upstanding elements that can engage with loop fibers and/or by increasing the holding power of each such engagement. Also, starting with a higher pin density (density of upstanding elements) before stretching will result in a density of upstanding elements after stretching that may be comparable to conventional mechanical fasteners. For example, when the density of upstanding elements is 550/cm$^2$ (3500/in$^2$), stretching to a ratio of about 2:1 results in a density of upstanding elements of about 248/cm$^2$ (1600/in$^2$), which is a conventional pin density for mechanical fasteners. Stretching a thermoplastic backing with upstanding elements provides stretched-induced molecular orientation at least in the backing.

For embodiments in which the thermoplastic backing is stretched, stretching can be carried out on a web biaxially or monoaxially using techniques known in the art. When the thermoplastic backing is a web of indefinite length, for example, monoaxial stretching in the machine direction can be performed by propelling the thermoplastic web over rolls of increasing speed. The most versatile stretching method that allows for monoaxial, sequential biaxial, and simultaneous biaxial stretching of a thermoplastic web employs a flat film tenter apparatus. Such an apparatus grasps the thermoplastic web using a plurality of clips, grippers, or other film edge-grasping means along opposing edges of the thermoplastic web in such a way that monoaxial, sequential biaxial, or simultaneous biaxial stretching in the desired direction is obtained by propelling the grasping means at varying speeds along divergent rails. Increasing clip speed in the machine direction generally results in machine-direction stretching. Means such as diverging rails generally results in cross-direction stretching. Monoaxial and biaxial stretching can be accomplished, for example, by the methods and apparatus disclosed in U.S. Pat. Appl. Pub. No. 2005/0202205 (Petersen et al.) and the references cited therein. Flat film tenter stretching apparatuses are commercially available, for example, from Bruckner Maschinenbau GmbH, Siegsdorf, Germany.

In some embodiments, the stretching increases at least one of the thermoplastic backing's length or width at least 1.5 times (in some embodiments, at least 2, 2.5, or 3 times). In some embodiments, the stretching increases both of the thermoplastic backing's length and width at least 1.5 times (in some embodiments, at least 2, 2.5, or 3 times). In some embodiments, the stretching increases at least one of the thermoplastic backing's length or width up to 10 times (in some embodiments, up to 7 or 5 times). In some embodiments, the stretching increases both of the thermoplastic backing's length and width up to 10 times (in some embodiments, up to 7 or 5 times).

The stretching can be adjusted to maximize desired product properties (e.g. engagement with a desired loop). In some embodiments, the stretching is carried out at least to the natural stretch ratio. When a thermoplastic film (e.g., a thermoplastic backing as described herein) is monoaxially or biaxially stretched at a temperature below the melting point of the thermoplastic material, particularly at a temperature below the line drawing temperature of the film, the thermoplastic film may stretch non-uniformly, and a clear boundary is formed between stretched and unstretched parts. This phenomenon is referred to as necking or line drawing. However, substantially the entire thermoplastic backing is stretched uniformly when it is stretched to a sufficiently high degree. The stretch ratio at which this occurs is referred to as the "natural stretch ratio" or "natural draw ratio." The natural stretch ratio may be defined, for example, as the stretch ratio where the relative standard deviation of local stretch ratios measured at a variety of locations on the thermoplastic backing is below about 15 percent. Stretching above the natural stretch ratio is understood to provide significantly more uniform properties or characteristics such as thickness, tensile strength, and modulus of elasticity. For any given thermoplastic backing and stretch conditions, the natural stretch ratio is determined by factors such as the composition of the thermoplastic resin forming the thermoplastic backing, the morphology of the formed thermoplastic backing due to quenching conditions on the tool roll, for example, and temperature and rate of stretching. Furthermore, for biaxially stretched thermoplastic backings, the natural stretch ratio in one direction will be affected by the stretch conditions, including final stretch ratio, in the other direction. Thus, there may be said to be a natural stretch ratio in one direction given a fixed stretch ratio in the other, or, alternatively, there may be said to be a pair of stretch ratios (one in the first direction and one in the second direction) which result in the natural stretch ratio. The term "stretch ratio" refers to ratio of a linear dimension of a given portion of the thermoplastic backing after stretching to the linear dimension of the same portion before stretching.

In some embodiments, stretching is performed at elevated temperatures. This may allow the thermoplastic backing to be more flexible for stretching. Heating can be provided, for example, by IR irradiation, hot air treatment or by performing the stretching in a heat chamber. In some embodiments, heating is only applied to the second surface of the thermoplastic backing (i.e., the surface opposite the surface from which the upstanding elements project) to minimize any damage to the capped stems that may result from heating. For example, in these embodiments, only rollers that are in contact with the second surface of the thermoplastic backing are heated.

After stretching, the thickness of the thermoplastic backing is decreased so that the ratio of the thickness of the thermoplastic backing before stretching to the thickness of the thermoplastic backing after stretching can be, for example, from 2:1 or 3:1 to 10:1, in some embodiments, from 5:1 to 10:1. The thickness of the thermoplastic backing may be, for example, in a range from 5 to 200 µm, 10 to 100 µm, or 30 to 70 µm.

After stretching, the final density of the upstanding elements is less than the initial density of the upstanding elements. In some embodiments of the method of making a structured surface according to the present disclosure, the upstanding elements have a final density (i.e., after stretching) of at least $20/cm^2$ ($129/in^2$), $40/cm^2$ ($258/in^2$), $60/cm^2$ ($387/in^2$), $75/cm^2$ ($484/in^2$), $100/cm^2$ ($645/in^2$), or $124/cm^2$ ($800/in^2$). For example, the final density of the upstanding elements may be at least $248/cm^2$ ($1600/in^2$) or at least about $394/cm^2$ ($2500/in^2$). In some embodiments, the final density of the upstanding elements may be up to $787/cm^2$ ($5000/in^2$) or up to about $1182/cm^2$ ($7500/in^2$). Final densities in a range from $124/cm^2$ ($800/in^2$) to $1182$ $cm^2$ ($7500/in^2$), $124/cm^2$ ($800/in^2$) to $787/cm^2$ ($5000/in^2$), and $124/cm^2$ ($800/in^2$) to $394/cm^2$ ($2500/in^2$) may be useful, for example. Again, the spacing of the upstanding elements need not be uniform.

For any of the embodiments of methods of making a structured surface or a structured surface disclosed herein, the thermoplastic backing may be in the form of a roll, from which patches of the structured surface (e.g., mechanical fastener patches) may be cut in a size appropriate to the desired application. In this application, the thermoplastic backing may also be a patch that has been cut to a desired size. In some of these embodiments, the second surface of the thermoplastic backing (i.e., the surface opposite the first surface from which the upstanding elements project) may be coated with an adhesive (e.g., a pressure sensitive adhesive). In such embodiments, when the thermoplastic backing is in the form of a roll, a release liner may be applied to the exposed adhesive.

In some embodiments of the method of making a structured surface disclosed herein, the thermoplastic backing is not joined to a carrier, at least when it is initially formed. When the backing is not joined to a carrier, it may mean that the backing is not laminated (e.g., extrusion laminated), adhered, bonded (e.g., ultrasonic bonded or compression bonded) or otherwise attached to a carrier (e.g., a substrate, fastening tab, fastening tape, etc.). In other embodiments, the method further comprises joining a second surface of the thermoplastic backing (i.e., the surface opposite the first surface from which the upstanding elements project) to a carrier. The thermoplastic backing may be joined to a carrier, for example, by lamination (e.g., extrusion lamination), adhesives (e.g., pressure sensitive adhesives), or other bonding methods (e.g., ultrasonic bonding, compression bonding, or surface bonding). Such joining methods may be carried out before contacting the overhanging portions of the distal caps with the implement, after contacting the overhanging portions of the distal caps with the implement, or before or after optionally stretching the thermoplastic backing, as desired. The thermoplastic backing may be joined to a carrier during the formation of the thermoplastic backing with upstanding stems. In embodiments where the method includes slitting the thermoplastic backing before the backing is joined to a carrier with a pressure sensitive adhesive, the viscosity of the pressure sensitive adhesive may be selected so that it does not go through the slits during the joining process. The article resulting from joining the structured surface to a carrier may be a fastening laminate, for example, a fastening tab joined to the backsheet of an absorbent article useful for joining the front waist region and the rear waist region of an absorbent article.

The carrier may be continuous (i.e., without any through-penetrating holes) or discontinuous (e.g. comprising through-penetrating perforations or pores). The carrier may comprise a variety of suitable materials including woven webs, nonwoven webs (e.g., spunbond webs, spunlaced webs, airlaid webs, meltblown web, and bonded carded webs), textiles, plastic films (e.g., single- or multilayered films, coextruded films, laterally laminated films, or films comprising foam layers), and combinations thereof. In some embodiments, the carrier is a fibrous material (e.g., a woven, nonwoven, or knit material). In some embodiments, the carrier comprises multiple layers of nonwoven materials with, for example, at least one layer of a meltblown nonwoven and at least one layer of a spunbonded nonwoven, or any other suitable combination of nonwoven materials. For example, the carrier may be a spunbond-meltbond-spunbond, spunbond-spunbond, or spunbond-spunbond-spunbond multilayer material. Or, the carrier may be a composite web comprising a nonwoven layer and a dense film layer.

Fibrous materials that provide useful carriers may be made of natural fibers (e.g., wood or cotton fibers), synthetic fibers (e.g., thermoplastic fibers), or a combination of natural and synthetic fibers. Exemplary materials for forming thermoplastic fibers include polyolefins (e.g., polyethylene, polypropylene, polybutylene, ethylene copolymers, propylene copolymers, butylene copolymers, and copolymers and blends of these polymers), polyesters, and polyamides. The fibers may also be multi-component fibers, for example, having a core of one thermoplastic material and a sheath of another thermoplastic material.

Useful carriers may have any suitable basis weight or thickness that is desired for a particular application. For a fibrous carrier, the basis weight may range, e.g., from at least about 20, 30, or 40 grams per square meter, up to about 400, 200, or 100 grams per square meter. The carrier may be up to about 5 mm, about 2 mm, or about 1 mm in thickness and/or at least about 0.1, about 0.2, or about 0.5 mm in thickness.

One or more zones of the carrier may comprise one or more elastically extensible materials extending in at least one direction when a force is applied and returning to approximately their original dimension after the force is removed. However, in some embodiments, including embodiments wherein the implement cuts through the thermoplastic backing, at least the portion of the carrier joined to the second face of the backing is not stretchable. In some embodiments, the portion of carrier joined to the second face of the backing will have up to a 10 (in some embodiments, up to 9, 8, 7, 6, or 5) percent elongation in the cross direction in the direction perpendicular to the slits through the backing.

The fastening laminate that can be formed after joining the thermoplastic backing to a carrier may be useful, for example, in absorbent articles. Exemplary absorbent articles have at least a front waist region, a rear waist region, and a longitudinal center line bisecting the front waist region and the rear waist region, wherein at least one of the front waist region or the rear waist region comprises the structured surface made according to the method disclosed herein. The fastening laminate may be in the form of a fastening tab that is bonded to at least one of the front waist region or the rear waist region extending outwardly from at least one of the left longitudinal edge or the right longitudinal edge of the absorbent article. In other embodiments, the fastening laminate may be an integral ear portion of the absorbent article.

Fastening laminates for use in absorbent articles may have any useful shape and size. A fastening tab may have a manufacturer's end that is attached to the disposable absorbent article (i.e., the end that is permanently fixed to the absorbent article, usually in the waist region) and a user's end that is distal from the point of attachment (i.e., the end that is grasped by the user). In some embodiments, the user's end can be narrower than the manufacturer's end. In these embodiments and others, it may be useful to differentially treat the upstanding elements at different locations of the fastening tab. For example, implements may be passed between each row at the user's end, while toward the manufacturing there may be multiple rows between implements. This tailoring may be particularly advantageous, for example, to improve the peel performance at the narrower edge, where there are fewer upstanding elements to engage a loop.

The fastening laminate may also be useful, for example, for disposable articles such as sanitary napkins. A sanitary napkin typically includes a back sheet that is intended to be placed adjacent to the wearer's undergarment. The back sheet may comprise a thermoplastic backing with upstanding elements to securely attach the sanitary napkin to the undergarment, which mechanically engages with the distal caps.

In some embodiments of the absorbent articles according to the present disclosure (e.g., diapers or other incontinence garments), the article further comprises a loop material to engage with the structured surface disclosed herein. The loop material may be provided, for example, as the back sheet of the absorbent articles, or loop patches can be provided as landing zones in either the front waist region or rear waist region. Loop can be made from any suitable material that interlocks with corresponding hook fastening elements. In some embodiments, the loop material is a knitted, woven, or non-woven fabric. For example, fiber loops may protrude from a knitted, woven, or non-woven backing or may be extrusion-bonded, adhesive-bonded, and/or sonically-bonded fiber loops. Suitable commercially available loop materials include knitted and extrusion-bonded loop materials from 3M Company, St. Paul, Minn. In some embodiments, the absorbent article according to the present disclosure includes an extrusion bonded loop. In some embodiments, the absorbent article according to the present disclosure includes a nonwoven loop.

In some embodiments where the carrier is a fibrous web, the joining comprises impinging heated gaseous fluid (e.g., ambient air, dehumidified air, nitrogen, an inert gas, or other gas mixture) onto a first surface of the fibrous web while it is moving; impinging heated fluid onto the second surface of the backing while the continuous web is moving, wherein the second surface is opposite the first surface of the backing; and contacting the first surface of the fibrous web with the second surface of the backing so that the first surface of the fibrous web is melt-bonded (e.g., surface-bonded or bonded with a loft-retaining bond) to the second surface of the backing. Impinging heated gaseous fluid onto the first surface of the fibrous web and impinging heated gaseous fluid on the second surface of the backing may be carried out sequentially or simultaneously. The term "surface-bonded" when referring to the bonding of fibrous materials means that parts of fiber surfaces of at least portions of fibers are melt-bonded to the second surface of the backing opposite the upstanding elements, in such a manner as to substantially preserve the original (pre-bonded) shape of the second surface of the backing, and to substantially preserve at least some portions of the second surface of the backing in an exposed condition, in the surface-bonded area. Quantitatively, surface-bonded fibers may be distinguished from embedded fibers in that at least about 65% of the surface area of the surface-bonded fiber is visible above the second surface of the backing in the bonded portion of the fiber. Inspection from more than one angle may be necessary to visualize the entirety of the surface area of the fiber. The term "loft-retaining bond" when referring to the bonding of fibrous materials means a bonded fibrous material comprises a loft that is at least 80% of the loft exhibited by the material prior to, or in the absence of, the bonding process. The loft of a fibrous material as used herein is the ratio of the total volume occupied by the web (including fibers as well as interstitial spaces of the material that are not occupied by fibers) to the volume occupied by the material of the fibers alone. If only a portion of a fibrous web has the second surface of the backing bonded thereto, the retained loft can be easily ascertained by comparing the loft of the fibrous web in the bonded area to that of the web in an unbonded area. It may be convenient in some circumstances to compare the loft of the bonded web to that of a sample of the same web before being bonded, for example, if the entirety of fibrous web has the second surface of the backing bonded thereto.

Further methods and apparatus for joining a continuous web to a fibrous carrier web using heated gaseous fluid may be found in co-pending U.S. patent applications with Ser.

Nos. 12/974,536 and 12/974,329, both filed Dec. 21, 2010, and incorporated herein by reference in their entirety.

Selected Embodiments of the Disclosure

In a first embodiment, the present disclosure provides a method of making a structured surface, the method comprising:
providing a thermoplastic backing with multiple rows of upstanding elements, the upstanding elements comprising stems with proximal ends attached to the thermoplastic backing and distal caps, wherein each distal cap has an overhanging portion that extends beyond the stem in a first direction; and
for at least some of the multiple rows, passing an implement between two adjacent rows, wherein the implement contacts the overhanging portion of at least some of the distal caps in the two adjacent rows such that at least part of the overhanging portion is turned in a second direction, different from the first direction.

In a second embodiment, the present disclosure provides the method of the first embodiment, wherein the implement does not cut through the thermoplastic backing.

In a third embodiment, the present disclosure provides the method of the first or second embodiment, wherein the implement is a needle, wire, or shim.

In a fourth embodiment, the present disclosure provides the method of any one of the first to third embodiments, wherein the implement is tapered.

In a fifth embodiment, the present disclosure provides the method of any one of the first to fourth embodiments, further comprising stretching the thermoplastic backing in at least one direction.

In a sixth embodiment, the present disclosure provides the method of the first embodiment, wherein the implement is a rotary cutter.

In a seventh embodiment, the present disclosure provides the method of any one of the first to sixth embodiments, further comprising heating at least one of the implement or the upstanding elements.

In an eighth embodiment, the present disclosure provides the method of any one of the first to sixth embodiments, wherein the method does not include heating the implement or the upstanding elements.

In a ninth embodiment, the present disclosure provides the method of any one of the first to eighth embodiments, wherein when at least part of the overhanging portion is turned in a second direction, it is turned toward the thermoplastic backing.

In a tenth embodiment, the present disclosure provides the method of any one of the first to ninth embodiments, wherein multiple implements are passed between the multiple rows simultaneously.

In an eleventh embodiment, the present disclosure provides the method of the tenth embodiment, wherein at least some of the multiple implements have different lengths or are positioned such that their tips are not aligned with each other.

In a twelfth embodiment, the present disclosure provides the method of the tenth or eleventh embodiment, wherein the multiple implements self-align between the multiple rows of upstanding elements.

In a thirteenth embodiment, the present disclosure provides the method of any one of the tenth to twelfth embodiments, wherein the multiple implements are positioned in a tool comprising a template structured surface, wherein the template structured surface comprises a template thermoplastic backing with multiple rows of template upstanding elements, the template upstanding elements comprising stems with proximal ends attached to the template thermoplastic backing and distal tips, and wherein the multiple implements are positioned between the multiple rows of the template upstanding elements on the template structured surface.

In a fourteenth embodiment, the present disclosure provides the method of the thirteenth embodiment, wherein the multiple rows of the template upstanding elements have the same spatial configuration as the multiple rows of upstanding elements on the thermoplastic backing.

In a fifteenth embodiment, the present disclosure provides the method of any one of the first to fourteenth embodiments, wherein the thermoplastic backing has an x-direction and a y-direction orthogonal to the x-direction, wherein the distal caps have overhanging portions extending beyond the stem in both the x-direction and the y-direction, and wherein the overhanging portions extending in only one of the x-direction or the y-direction are turned in the second direction.

In a sixteenth embodiment, the present disclosure provides the method of the fifteenth embodiment, wherein the distal caps are round before passing the implement between the two adjacent rows.

In a seventeenth embodiment, the present disclosure provides the method of the fifteenth embodiment, wherein the distal caps are oval before passing the implement between the two adjacent rows.

In an eighteenth embodiment, the present disclosure provides the method of the fifteenth or sixteenth embodiment, wherein overhanging portions extend beyond the stem on all sides and are substantially equivalent in volume.

In a nineteenth embodiment, the present disclosure provides the method of any one of the first to eighteenth embodiments, wherein the structured surface is a mechanical fastener.

In a twentieth embodiment, the present disclosure provides the method of any one of the first to nineteenth embodiments, wherein the implement is positioned at a 15 degree to 45 degree angle to the thermoplastic backing.

In a twenty-first embodiment, the present disclosure provides the method of any one of the first to twentieth embodiments, wherein the thermoplastic backing is a web of indefinite length having a machine direction and a cross direction.

In a twenty-second embodiment, the present disclosure provides the method of the twenty-first embodiment, wherein only the overhanging portions extending in the cross direction are turned in the second direction.

In a twenty-third embodiment, the present disclosure provides the method of any one of the first to twenty-second embodiments, wherein the thermoplastic backing has a second surface opposite the upstanding elements, the method further comprising joining the second surface of the backing to a carrier.

In a twenty-fourth embodiment, the present disclosure provides a structured surface comprising:
a thermoplastic backing having an x-direction and a y-direction; and
upstanding elements comprising stems with proximal ends attached to the thermoplastic backing and distal caps, wherein each distal cap has overhanging portions that extend beyond the stem on all sides, wherein overhanging portions extending beyond the stem on all sides are substantially equivalent in volume, and wherein for at least some of the upstanding elements the overhanging portions extending in only one of the x-direction or the y-direction are turned down toward the thermoplastic backing.

In a twenty-fifth embodiment, the present disclosure provides the structured surface of the twenty-fourth embodiment, wherein for the at least some of the upstanding elements all of the overhanging portions are rounded.

In a twenty-sixth embodiment, the present disclosure provides the structured surface of the twenty-fourth or twenty-fifth embodiment, wherein the upstanding elements are aligned in rows on the thermoplastic backing.

In a twenty-seventh embodiment, the present disclosure provides the structured surface of any one of the twenty-fourth to twenty-sixth embodiments, wherein the thermoplastic backing is a web of indefinite length having a machine direction and a cross direction, wherein the y-direction is the machine direction, wherein the x-direction is the cross direction, and wherein only the overhanging portions extending in the cross direction are turned down toward the thermoplastic backing.

In a twenty-eighth embodiment, the present disclosure provides a fastening laminate comprising a carrier and the structured surface of any one of the twenty-fourth to twenty-seventh embodiments, wherein the thermoplastic backing has a second surface opposite the upstanding elements, and wherein the second surface of the backing is joined to the carrier.

In a twenty-ninth embodiment, the present disclosure provides an absorbent article having at least a front waist region, a rear waist region, and a longitudinal center line bisecting the front waist region and the rear waist region, wherein at least one of the front waist region or the rear waist region comprises a fastening laminate according to embodiment 28.

In a thirtieth embodiment, the present disclosure provides a tool for shaping distal caps on upstanding elements on a structured surface, the tool comprising a template structured surface and multiple implements, the template structured surface comprising a template thermoplastic backing with multiple rows of template upstanding elements, wherein the template upstanding elements comprise stems with proximal ends attached to the template thermoplastic backing and distal tips, and wherein the multiple implements are positioned between the multiple rows of the template upstanding elements on the template structured surface.

In a thirty-first embodiment, the present disclosure provides the tool of embodiment 30, wherein the multiple implements comprise at least one of needles, wires, or shims.

In order that this disclosure can be more fully understood, the following examples are set forth. It should be understood that these examples are for illustrative purposes only, and are not to be construed as limiting this disclosure in any manner.

EXAMPLES

Hook Strips

The hook strips of Comparative Examples 1-4A (available under the product number listed in Table 1 from the 3M Company, St. Paul, Minn.) were prepared using the method described in U.S. Pat. No. 5,845,375 (Miller et al.). The polymer used to prepare the hook strips was an ethylene-propylene copolymer available from Dow Chemical Co., Midland, Mich., under the trade designation "C700-35N". The hook density was 1600 hooks per square inch (248 cm$^2$) arranged in a square array and the post shape was conical. In Table 1, the total caliper, base film caliper, basis weight, cap diameter in the CD direction, and cap diameter in the MD direction are recorded for Comparative Examples 1-4A. The cap shapes for Comparative Examples 1 and 2 were oval. The cap shapes for Comparative Examples 3, 4, and 4A were round. Comparative Example 4A was prepared from Comparative Example 4 using the procedure described in U.S. Pat. No. 6,132,660 to form "hook heads with downwardly projecting fiber engaging portions".

TABLE 1

| Example | Base Film Caliper (μm) | Cap Diameter in CD (μm) | Cap Diameter in MD (μm) | Total Caliper (μm) | Basis Weight (gsm) |
|---|---|---|---|---|---|
| Comparative Example 1 | 85 | 420 | 300 | 430 | 104 |
| Comparative Example 2 | 85 | 350 | 250 | 470 | 104 |
| Comparative Example 3 | 100 | 350 | 350 | 440 | 117 |
| Comparative Example 4 | 180 | 350 | 350 | 515 | 191 |
| Comparative Example 4A | 180 | 350 | 350 | 510 | 191 |

The hook strips of Examples 1-4 were prepared from the corresponding Comparative Examples (Table 2) using the apparatus described in FIG. 7. The implement portion 125 of the apparatus consisted of a 1 inch (2.54 cm) wide strip of 44 hypodermic syringe needles (25 gauge) that were spaced to align with the rows (MD direction) of the hook strips. The alignment was achieved by using the uncapped 1600 ppi (pins per square inch) (248/cm$^2$) stem web as a template for needle spacing. The needles were placed in the rows of the uncapped stem web and the bottom (flat) face of the stem web was attached to a 2.5 inch (6.35 cm) by 0.5 inch (1.27 cm) by 0.0625 inch (0.16 cm) piece of rubber using double sided tape. A second piece of rubber 105 with the same dimensions was placed on top of the needles and the resulting implement assembly was placed in a clamp 100 to provide the apparatus of FIG. 7. The needles extended a distance of approximately 0.75 inch (1.9 cm) from the edge of the clamp. The needles were placed in alignment with the rows of the hook strip and the apparatus was pulled by hand across the hook strip such that the angle formed between the implement portion of the apparatus and the hook strip backing (in the direction of the hand motion) was between approximately 15-45 degrees. The resulting change in hook shape (for example, from FIG. 8A to FIG. 8B) was independent of the angle used.

TABLE 2

| Example Number | Precursor Hook Strip |
|---|---|
| Example 1 | Comparative Example 1 |
| Example 2 | Comparative Example 2 |
| Example 3 | Comparative Example 3 |
| Example 4 | Comparative Example 4 |

Test Method and Test Results

The disengagement performance characteristics of the materials prepared as examples were measured using four different test methods. All testing was conducted at constant temperature (23° C.+/−2° C.) and constant relative humidity (50%+/−5%). All materials and equipment were equilibrated at these conditions for a minimum of 24 hours prior to testing. A universal constant rate of extension tensile testing instrument equipped with a computer for data recording and the required load ranges was used (Series 4200, 4500, or 5500 available from Instron Engineering Corporation, Canton, Mass.). The instrument crosshead speed was set to 12 inches (30.5 cm)/minute for all tests.

The extrusion bonded loop (EBL) and nonwoven loop samples were obtained by removing loop fastener patches from commercially available baby diapers. The EBL samples [described in U.S. Pat. No. 5,256,231 (Gorman et al.)] were obtained from New Baby Size 1 diapers available from Procter & Gamble Company, Cincinnati, Ohio under the trade designation "PAMPERS SWADDLERS". The nonwoven loop samples were obtained from size 4 baby diapers (available from Procter & Gamble Company) under the trade designation "LUVS". The nylon knitted loop samples had a fabric basis weight of about 22 grams per square meter (gsm) and were backed with a film of biaxially oriented polypropylene (BOPP, basis weight of about 11 gsm).

In Test Method 1, the force required to peel the hook material from the loop material at a 180 degree peel angle with shear engagement was measured. The finished hook samples were prepared as a 0.5 inch (1.27 cm) Cross Direction (CD) by 1 inch (2.54 cm) Machine Direction (MD) strip with fastening tape used as the backing material. The hook sample was attached approximately in the center of a 1 inch (2.54 cm) by 8 inch (20.32 cm) paper leader. The leader was folded in half away from the hook, so as to apply a shear engagement with one end and a 180 degree peel with the other. The finished loop element was cut to at least 3 inch (7.62 cm) CD by 2 inch (5.08 cm) MD. The hook sample was gently placed hook side down onto the corresponding loop face and secured with one cycle (one cycle=one forward and one backward pass) of a 4.5 pound (2.0 kg) hand held roller. The shear engagement was conducted by hanging a 500 g mass from the finished assembly for 10 seconds. The 180 degree peel end of the leader was attached to the lower jaw while the loop was attached, vertically aligned to the leader, in the upper jaw of the Instron instrument, allowing for a slight amount of slack. The materials were oriented so that the peel was conducted in the hook CD and the loop CD. The initial jaw separation (gauge length) was set to 3 inches (7.62 cm). The instrument was started and the upper jaw traveled until the hook sample was completely disengaged from the loop sample. Measurements were taken of the maximum load (Max. Load), average load (Avg. Load), and average peak load (Avg. Peak) in units of gram-force (gf). The data collected from ten replicates, each using fresh materials, was averaged and the averaged data is reported in Tables 3-5 along with the corresponding standard deviation values.

TABLE 3

CD Peel with EBL as the Loop Substrate

| Example | Max. Load (gf) | Max. Load (StDev) | Avg. Load (gf) | Avg. Load (StDev) | Avg. Peak (gf) | Avg. Peak (StDev) |
|---|---|---|---|---|---|---|
| Comparative Example 1 | 1223 | 145 | 470 | 41 | 590 | 112 |
| Example 1 | 1103 | 218 | 453 | 58 | 516 | 104 |
| Comparative Example 2 | 734 | 144 | 191 | 47 | 206 | 61 |
| Example 2 | 902 | 204 | 324 | 92 | 434 | 152 |
| Comparative Example 3 | 463 | 249 | 124 | 62 | 147 | 93 |
| Example 3 | 1248 | 174 | 449 | 76 | 558 | 160 |
| Comparative Example 4 | 437 | 216 | 94 | 47 | 98 | 76 |
| Comparative Example 4A | 1586 | 144 | 424 | 78 | 478 | 269 |
| Example 4 | 1489 | 349 | 418 | 111 | 763 | 532 |

TABLE 4

CD Peel with Knitted Loop as the Loop Substrate

| Example | Max. Load (gf) | Max. Load (StDev) | Avg. Load (gf) | Avg. Load (StDev) | Avg. Peak (gf) | Avg. Peak (StDev) |
|---|---|---|---|---|---|---|
| Comparative Example 1 | 252 | 73 | 88 | 28 | 123 | 39 |
| Example 1 | 199 | 34 | 61 | 12 | 90 | 19 |
| Comparative Example 2 | 112 | 52 | 28 | 13 | 49 | 29 |
| Example 2 | 131 | 58 | 32 | 13 | 55 | 25 |
| Comparative Example 3 | 172 | 35 | 53 | 14 | 79 | 23 |
| Example 3 | 281 | 178 | 68 | 38 | 127 | 76 |
| Comparative Example 4 | 241 | 80 | 75 | 21 | 127 | 41 |
| Comparative Example 4A | 207 | 61 | 71 | 20 | 107 | 30 |
| Example 4 | 304 | 122 | 72 | 31 | 148 | 66 |

TABLE 5

CD Peel with Nonwoven Loop as the Loop Substrate

| Example | Max. Load (gf) | Max. Load (StDev) | Avg. Load (gf) | Avg. Load (StDev) | Avg. Peak (gf) | Avg. Peak (StDev) |
|---|---|---|---|---|---|---|
| Comparative Example 1 | 286 | 75 | 130 | 32 | 166 | 46 |
| Example 1 | 129 | 39 | 64 | 19 | 79 | 24 |
| Comparative Example 2 | 269 | 82 | 88 | 35 | 134 | 56 |
| Example 2 | 197 | 57 | 93 | 19 | 118 | 28 |
| Comparative Example 3 | 214 | 49 | 72 | 19 | 100 | 27 |
| Example 3 | 180 | 37 | 77 | 17 | 102 | 20 |
| Comparative Example 4 | 248 | 105 | 72 | 24 | 102 | 34 |
| Comparative Example 4A | 127 | 50 | 50 | 17 | 64 | 21 |
| Example 4 | 138 | 46 | 63 | 19 | 80 | 25 |

In Test Method 2, the diaper ear fastening tabs were removed from a "Parents Choice" size 4 diaper (available from Walmart Corporation, Bentonville, Ark.) and labeled to identify the position of attachment (located on right or left side of the diaper). The existing hook material on each fastening tab was removed from the nonwoven carrier of the fastening tab. This was done by cooling the tabs thru exposure to liquid nitrogen and peeling the existing hook pieces off of the nonwoven carrier while cold. The nonwoven carrier was warmed to room temperature and a hook strip selected from Comparative Examples 1-4A and Examples 1-4 (13 mm by 25.4 mm in size) was then placed on the nonwoven carrier of the diaper fastening tab using two layers of a double coated adhesive tape (available from the 3M Company, St. Paul, Minn., under the trade designation "SCOTCH ADHESIVE TRANSFER TAPE NO. 924"). The existing loop substrate was also removed using the same liquid nitrogen procedure described above. The test loop substrate (selected from the three loop samples described above) was attached to the diaper in the same position as the previously removed loop substrate using "3M SUPER 77 MULTIPURPOSE SPRAY ADHESIVE" (available from the 3M Company, St. Paul, Minn.). The test loop substrate was labeled to identify the right and left sides of the diaper. The landing zone area containing the test loop substrate was then cut off of the diaper approximately 0.5 inches (1.27 cm) to 0.75 inches (1.9 cm) below the landing zone area. The diaper ear fastening tabs (containing hook material selected from the Comparative Examples 1-4A and Examples 1-4) were matched to the corresponding loop substrate (right side or left side of the diaper) and placed hook side down on the loop substrate. Each hook strip was gently rubbed one time in the machine direction and then further secured with two cycles (one cycle=one forward and one backward pass) of a one pound hand roller moving in the machine direction of the hook. The time for one cycle was approximately two seconds. The landing zone was cut in the middle yielding two prepared test samples. The finger lift portion of the hook fastening tab was inserted in the upper jaw of the Instron instrument, while the loop substrate was placed in the lower jaw. The materials were oriented so that the peel was conducted in the hook CD and the loop CD. The initial jaw separation (gauge length) was set to 1-2 inches (2.54-5.1 cm). The instrument was started and the upper jaw traveled until the hook sample was completely disengaged from the loop sample. Measurements were taken of the maximum load (Max. Load), average load (Avg. Load), and average peak load (Avg. Peak) in units of gram-force (gf). The data collected from five replicates, each using fresh materials, was averaged and the averaged data is reported in Tables 6-8 along with the corresponding standard deviation values.

TABLE 6

CD Peel with EBL as the Loop Substrate

| Example | Max. Load (gf) | Max. Load (StDev) | Avg. Load (gf) | Avg. Load (StDev) | Avg. Peak (gf) | Avg. Peak (StDev) |
|---|---|---|---|---|---|---|
| Comparative Example 1 | 934 | 241 | 600 | 147 | 691 | 171 |
| Example 1 | 1089 | 124 | 705 | 103 | 814 | 133 |
| Comparative Example 2 | 887 | 187 | 512 | 138 | 616 | 184 |
| Example 2 | 1098 | 169 | 669 | 43 | 765 | 80 |
| Comparative Example 3 | 1126 | 225 | 516 | 103 | 611 | 122 |
| Example 3 | 1079 | 153 | 661 | 104 | 776 | 91 |
| Comparative Example 4 | 892 | 352 | 294 | 104 | 354 | 80 |
| Comparative Example 4A | 1314 | 487 | 604 | 222 | 673 | 169 |
| Example 4 | 1559 | 475 | 671 | 109 | 685 | 91 |

TABLE 7

CD Peel with Knitted Loop as the Loop Substrate

| Example | Max. Load (gf) | Max. Load (StDev) | Avg. Load (gf) | Avg. Load (StDev) | Avg. Peak (gf) | Avg. Peak (StDev) |
|---|---|---|---|---|---|---|
| Comparative Example 1 | 218 | 89 | 79 | 39 | 98 | 57 |
| Example 1 | 237 | 96 | 96 | 41 | 121 | 59 |
| Comparative Example 2 | 155 | 79 | 62 | 32 | 68 | 40 |
| Example 2 | 183 | 50 | 84 | 21 | 99 | 27 |
| Comparative Example 3 | 255 | 49 | 95 | 19 | 114 | 33 |
| Example 3 | 191 | 44 | 44 | 23 | 45 | 25 |
| Comparative Example 4 | 220 | 118 | 61 | 23 | 69 | 29 |
| Comparative Example 4A | 270 | 77 | 96 | 26 | 126 | 34 |
| Example 4 | 273 | 102 | 71 | 21 | 70 | 30 |

TABLE 8

CD Peel with Nonwoven Loop as the Loop Substrate

| Example | Max. Load (gf) | Max. Load (StDev) | Avg. Load (gf) | Avg. Load (StDev) | Avg. Peak (gf) | Avg. Peak (StDev) |
|---|---|---|---|---|---|---|
| Comparative Example 1 | 305 | 46 | 199 | 39 | 223 | 47 |
| Example 1 | 294 | 28 | 168 | 42 | 179 | 45 |
| Comparative Example 2 | 396 | 66 | 238 | 54 | 276 | 38 |
| Example 2 | 386 | 100 | 148 | 42 | 192 | 68 |
| Comparative Example 3 | 301 | 55 | 171 | 62 | 200 | 66 |
| Example 3 | 412 | 91 | 237 | 73 | 254 | 85 |
| Comparative Example 4 | 329 | 185 | 97 | 71 | 94 | 69 |
| Comparative Example 4A | 350 | 88 | 172 | 26 | 191 | 37 |
| Example 4 | 453 | 83 | 202 | 49 | 207 | 65 |

In Test Method 3, the diaper ear fastening tabs were removed from a "Parents Choice" size 4 diaper (available from Walmart Corporation, Bentonville, Ark.) and labeled to identify the position of attachment (located on right or left side of the diaper). The existing hook material on each fastening tab was removed from the nonwoven carrier of the fastening tab. This was done by cooling the tabs thru exposure to liquid nitrogen and peeling the existing hook pieces off of the nonwoven carrier while cold. The nonwoven carrier was warmed to room temperature and a hook strip selected from Comparative Examples 1-4A and Examples 1-4 (13 mm by 25.4 mm in size) was then placed on the nonwoven carrier of the diaper fastening tab using two layers of a double coated adhesive tape (available from the 3M Company, St. Paul, Minn., under the trade designation "SCOTCH ADHESIVE TRANSFER TAPE NO. 924"). The existing loop substrate was also removed using the same liquid nitrogen procedure described above. The test loop substrate (selected from the three loop samples described above) was attached to the diaper in the same position as the previously removed loop substrate using "3M SUPER 77 MULTIPURPOSE SPRAY ADHESIVE" (available from the 3M Company, St. Paul, Minn.). The test loop substrate was labeled to identify the right or left side of the diaper. The landing zone area containing the test loop substrate was then cut off of the diaper approximately 0.5 inches (1.3 cm) to 0.75 inches (1.9 cm) below the landing zone area. The portion of the ear fastening tab containing hook material was carefully cut from the fastening tab and then attached approximately in the center of a paper leader (1 inch by 3 inch, 2.54 cm by 7.62 cm). The attachment was made with a staple. The staple was positioned close to the top edge of the hook strip with the flat side of the staple located on the hook face. The hook strips were matched to the corresponding loop substrate (right side or left side of the diaper) and placed hook side down on the loop substrate. Each hook strip was gently rubbed one time in the machine direction and then further secured with two cycles (one cycle=one forward and one backward pass) of a one pound hand roller moving in the machine direction of the hook. The time for one cycle was approximately two seconds. The landing zone was cut in the middle yielding two prepared test samples. The paper leader was inserted in the upper jaw of the Instron instrument, while the loop substrate was placed in the lower jaw. The materials were oriented so that the peel was conducted in the hook MD and the loop MD. The initial jaw separation (gauge length) was set to 1-2 inches (2.54-5.1 cm). The instrument was started and the upper jaw traveled until the hook sample was completely disengaged from the loop sample. Measurements were taken of the maximum load (Max. Load), average load (Avg. Load), and average peak load (Avg. Peak) in units of gram-force (gf). The data collected from five replicates, each using fresh materials, was averaged and the averaged data is reported in Tables 9-11 along with the corresponding standard deviation values.

TABLE 9

MD Peel with EBL as the Loop Substrate

| Example | Max. Load (gf) | Max. Load (StDev) | Avg. Load (gf) | Avg. Load (StDev) | Avg. Peak (gf) | Avg. Peak (StDev) |
|---|---|---|---|---|---|---|
| Comparative Example 1 | 306 | 150 | 193 | 89 | 207 | 92 |
| Example 1 | 339 | 79 | 225 | 59 | 245 | 69 |
| Comparative Example 2 | 84 | 29 | 44 | 12 | 47 | 12 |
| Example 2 | 178 | 44 | 109 | 26 | 117 | 29 |
| Comparative Example 3 | 264 | 115 | 128 | 58 | 137 | 69 |
| Example 3 | 379 | 82 | 233 | 43 | 261 | 54 |
| Comparative Example 4 | 85 | 33 | 36 | 15 | 39 | 18 |
| Comparative Example 4A | 443 | 170 | 267 | 68 | 294 | 79 |
| Example 4 | 316 | 75 | 191 | 36 | 206 | 43 |

TABLE 10

MD Peel with Knitted Loop as the Loop Substrate

| Example | Max. Load (gf) | Max. Load (StDev) | Avg. Load (gf) | Avg. Load (StDev) | Avg. Peak (gf) | Avg. Peak (StDev) |
|---|---|---|---|---|---|---|
| Comparative Example 1 | 113 | 43 | 39 | 29 | 43 | 34 |
| Example 1 | 167 | 54 | 60 | 14 | 63 | 19 |
| Comparative Example 2 | 84 | 23 | 20 | 3 | 23 | 3 |
| Example 2 | 76 | 23 | 17 | 4 | 17 | 7 |
| Comparative Example 3 | 58 | 21 | 17 | 10 | 20 | 11 |
| Example 3 | 68 | 22 | 22 | 12 | 23 | 11 |
| Comparative Example 4 | 41 | 10 | 14 | 8 | 15 | 8 |
| Comparative Example 4A | 107 | 71 | 35 | 17 | 37 | 21 |
| Example 4 | 62 | 22 | 28 | 13 | 28 | 15 |

TABLE 11

MD Peel with Nonwoven Loop as the Loop Substrate

| Example | Max. Load (gf) | Max. Load (StDev) | Avg. Load (gf) | Avg. Load (StDev) | Avg. Peak (gf) | Avg. Peak (StDev) |
|---|---|---|---|---|---|---|
| Comparative Example 1 | 194 | 39 | 111 | 13 | 114 | 14 |
| Example 1 | 168 | 24 | 120 | 20 | 125 | 22 |
| Comparative Example 2 | 72 | 14 | 33 | 5 | 37 | 5 |
| Example 2 | 124 | 37 | 72 | 32 | 74 | 34 |
| Comparative Example 3 | 82 | 22 | 47 | 19 | 50 | 19 |
| Example 3 | 202 | 46 | 132 | 35 | 140 | 39 |
| Comparative Example 4 | 56 | 18 | 21 | 11 | 21 | 11 |
| Comparative Example 4A | 202 | 14 | 123 | 23 | 129 | 28 |
| Example 4 | 168 | 39 | 99 | 24 | 103 | 27 |

In Test Method 4, the force required to disengage a mechanical fastener system after a minimal force was used to engage the hook and loop samples was measured. A 90 degree test jig capable of holding a 2 inch (5.1 cm) by 5 inch (12.7 cm) steel plate was inserted in the lower jaw of the Instron tensile tester. The bottom (flat) face of a 1 square inch (6.5 square cm) piece of finished hook sample (selected from Comparative Examples 1-4A and Examples 1-4) was attached with double sided adhesive tape (available from the 3M Company, St. Paul, Minn., under the trade designation "SCOTCH Double Coated TAPE NO. 9579") to the bottom of a 240 g test apparatus. The finished loop sample was attached with double sided tape so as to completely cover one side a 2 inch (5.1 cm) by 5 inch (12.7 cm) steel plate with the CD direction of the loop material oriented parallel to the long dimension of the panel. The plate containing loop sample was inserted into the 90 degree peel jig. The test apparatus containing the hook sample was inserted into the top Instron jaw and lightly set down onto the loop face being careful not to apply pressure. The initial jaw separation (gauge length) was set to 9.5 inches (24 cm). The instrument was started and the upper jaw traveled until the hook sample was completely disengaged from the loop sample. Measurement of the maximum load (Max. Load) was recorded in units of gram-force (gf). The data collected from ten replicates, each using fresh materials, was averaged and the averaged data is reported in Tables 12-14 along with the corresponding standard deviation values.

TABLE 12

90° Disengagement with EBL as the Loop Substrate

| Example | Max. Load (gf) | Max. Load (StDev) |
|---|---|---|
| Comparative Example 1 | 315 | 81 |
| Example 1 | 558 | 160 |
| Comparative Example 2 | 230 | 96 |
| Example 2 | 572 | 254 |
| Comparative Example 3 | 251 | 140 |
| Example 3 | 426 | 181 |
| Comparative Example 4 | 155 | 36 |
| Comparative Example 4A | 395 | 201 |
| Example 4 | 399 | 218 |

TABLE 13

90° Disengagement with Knitted Loop as the Loop Substrate

| Example | Max. Load (gf) | Max. Load (StDev) |
|---|---|---|
| Comparative Example 1 | 149 | 22 |
| Example 1 | 169 | 24 |
| Comparative Example 2 | 164 | 17 |
| Example 2 | 152 | 24 |

TABLE 13-continued

90° Disengagement with Knitted Loop as the Loop Substrate

| Example | Max. Load (gf) | Max. Load (StDev) |
|---|---|---|
| Comparative Example 3 | 189 | 29 |
| Example 3 | 203 | 19 |
| Comparative Example 4 | 173 | 43 |
| Comparative Example 4A | 227 | 35 |
| Example 4 | 234 | 59 |

TABLE 14

90° Disengagement with Nonwoven Loop as the Loop Substrate

| Example | Max. Load (gf) | Max. Load (StDev) |
|---|---|---|
| Comparative Example 1 | 199 | 57 |
| Example 1 | 289 | 67 |
| Comparative Example 2 | 200 | 51 |
| Example 2 | 207 | 60 |
| Comparative Example 3 | 188 | 54 |
| Example 3 | 242 | 80 |
| Comparative Example 4 | 175 | 28 |
| Comparative Example 4A | 303 | 65 |
| Example 4 | 199 | 28 |

This disclosure may take on various modifications and alterations without departing from its spirit and scope. Accordingly, this disclosure is not limited to the above-described embodiments but is to be controlled by the limitations set forth in the following claims and any equivalents thereof. This disclosure may be suitably practiced in the absence of any element not specifically disclosed herein. All patents and patent applications cited above are hereby incorporated by reference into this document in their entirety.

What is claimed is:

1. A method of making a structured surface, the method comprising:
   providing a web of a thermoplastic backing having a machine direction and a cross direction, the thermoplastic backing having multiple rows of upstanding elements, the upstanding elements comprising stems with proximal ends attached to the thermoplastic backing and distal caps, wherein each distal cap has an overhanging portion that extends beyond the stem in a first direction and a non-overhanging portion that does not extend beyond the stem; and
   while the web is moving in the machine direction causing multiple implements to pass between adjacent pairs of rows for at least some of the multiple rows, wherein each implement contacts the overhanging portion of at least some of the distal caps in the adjacent pairs of rows without contacting the non-overhanging portion, such that at least part of the overhanging portion is turned in a second direction, different from the first direction.

2. The method of claim 1, wherein each of the multiple implements does not cut through the thermoplastic backing.

3. The method of claim 1, wherein each of the multiple implements is a needle, wire, or shim.

4. The method of claim 1, wherein each of the multiple implements is tapered.

5. The method of claim 1, further comprising stretching the thermoplastic backing in at least one direction.

6. The method of claim 1, further comprising heating at least one of the multiple implements or the upstanding elements.

7. The method of claim 1, wherein when at least part of the overhanging portion is turned in a second direction, it is turned toward the thermoplastic backing.

8. The method of claim 1, wherein at least some of the multiple implements have different lengths or are positioned such that their tips are not aligned with each other.

9. The method of claim 1, wherein the multiple implements self-align between the multiple rows of upstanding elements.

10. The method of claim 1, wherein the distal caps have overhanging portions extending beyond the stem in both the cross direction and the machine direction, and wherein the overhanging portions extending in only the cross direction are turned in the second direction.

11. The method of claim 1, wherein the distal caps are round or oval before passing the implement between the two adjacent rows.

12. The method of claim 1, wherein the multiple implements are positioned in a tool comprising a template structured surface, wherein the template structured surface comprises a template thermoplastic backing with multiple rows of template upstanding elements, the template upstanding elements comprising stems with proximal ends attached to the template thermoplastic backing and distal tips, and wherein the multiple implements are positioned between the multiple rows of the template upstanding elements on the template structured surface.

13. The method of claim 12, wherein the multiple rows of the template upstanding elements have the same spatial configuration as the multiple rows of upstanding elements on the thermoplastic backing.

14. The method of claim 1, wherein the thermoplastic backing has a second surface opposite the upstanding elements, the method further comprising joining the second surface of the backing to a carrier.

15. The method of claim 1, wherein each of the multiple implements has a maximum width in the cross direction less than or equal to the spacing in the cross direction between the stems in a pair of adjacent rows.

16. The method of claim 1, wherein the multiple implements do not pass between every one of the multiple rows of upstanding elements.

17. The method of claim 1, wherein groups of the multiple implements contact the multiple rows of upstanding elements in a first zone of the thermoplastic backing while in a second zone upstanding elements are not contacted by the multiple implements.

18. The method of claim 1, wherein each of the multiple implements is a rotary cutter.

19. The method of claim 1, wherein each of the multiple implements is positioned at a 15 degree to 45 degree angle to the thermoplastic backing.

20. The method of claim 1, wherein the method does not include heating the multiple implements or the upstanding elements.

* * * * *